US010628509B2

(12) United States Patent
Skellenger et al.

(10) Patent No.: US 10,628,509 B2
(45) Date of Patent: Apr. 21, 2020

(54) AVATAR-BASED HEALTH PORTAL WITH MULTIPLE NAVIGATIONAL MODES

(71) Applicant: Human Longevity, Inc., San Diego, CA (US)

(72) Inventors: John Scott Skellenger, San Diego, CA (US); Yaron Turpaz, San Diego, CA (US)

(73) Assignee: HUMAN LONGEVITY, INC., San Diego, CA (US)

( * ) Notice: Subject to any disclaimer, the term of this patent is extended or adjusted under 35 U.S.C. 154(b) by 11 days.

(21) Appl. No.: 16/091,934

(22) PCT Filed: Apr. 5, 2017

(86) PCT No.: PCT/US2017/026148
§ 371 (c)(1),
(2) Date: Oct. 5, 2018

(87) PCT Pub. No.: WO2017/176884
PCT Pub. Date: Oct. 12, 2017

(65) Prior Publication Data
US 2019/0129910 A1 May 2, 2019

Related U.S. Application Data

(60) Provisional application No. 62/318,708, filed on Apr. 5, 2016.

(51) Int. Cl.
*G06F 3/048* (2013.01)
*G06F 16/954* (2019.01)
(Continued)

(52) U.S. Cl.
CPC .......... *G06F 16/954* (2019.01); *G06Q 10/06* (2013.01); *G06Q 10/10* (2013.01); *G06Q 50/22* (2013.01);
(Continued)

(58) Field of Classification Search
CPC ...... G06F 3/048; G06F 3/0481; G06F 3/0482; G06F 19/00; G06F 16/954; G06T 13/40;
(Continued)

(56) References Cited

U.S. PATENT DOCUMENTS 8,471,846 B2 * 6/2013 Kohlmann .............. G06T 19/00
345/419
2001/0051881 A1 * 12/2001 Filler .................. G06F 19/3418
705/3
(Continued)

FOREIGN PATENT DOCUMENTS

KR 10-20-150124422 A1 10/2015
KR 10-16-06155500 A1 3/2016

OTHER PUBLICATIONS

International Search Report—PCT/US2017/026148 dated Jun. 29, 2017.
(Continued)

*Primary Examiner* — Xiomara L Bautista
(74) *Attorney, Agent, or Firm* — McDermott Will & Emery LLP

(57) ABSTRACT

Systems, media, and methods for providing an interactive health portal for presentation of health information of an individual including: an animated three-dimensional avatar of the individual and at least one of the following distinct navigational modes for navigating a plurality of categories of health information, each category having at least one subcategory of health information, the modes including: a list navigational mode; a two-dimensional map navigational mode; and a three-dimensional landscape navigational mode; wherein the individual can switch between the navigational modes.

18 Claims, 23 Drawing Sheets

(51) Int. Cl.
*G16H 10/60* (2018.01)
*G06T 13/40* (2011.01)
*G06Q 50/22* (2018.01)
*G16H 50/30* (2018.01)
*G06Q 10/06* (2012.01)
*G06Q 10/10* (2012.01)
*G16H 15/00* (2018.01)
*G06T 19/00* (2011.01)

(52) U.S. Cl.
CPC ............ *G06T 13/40* (2013.01); *G06T 19/003* (2013.01); *G16H 10/60* (2018.01); *G16H 15/00* (2018.01); *G16H 50/30* (2018.01)

(58) Field of Classification Search
CPC ....... G06T 19/00; G06T 19/003; G16H 10/60; G16H 15/00
See application file for complete search history.

(56) References Cited

U.S. PATENT DOCUMENTS

| | | | |
|---|---|---|---|
| 2002/0111932 A1* | 8/2002 | Roberge | G06F 3/0482 |
| 2002/0116226 A1* | 8/2002 | Auer | G06F 19/321 |
| | | | 705/3 |
| 2003/0076351 A1* | 4/2003 | Ide | G06Q 30/02 |
| | | | 715/738 |
| 2005/0108051 A1* | 5/2005 | Knapheide | G06Q 50/22 |
| | | | 705/2 |
| 2006/0061595 A1* | 3/2006 | Goede | G06F 17/241 |
| | | | 345/619 |
| 2009/0254848 A1* | 10/2009 | Glaser-Seidnitzer | |
| | | | A61B 6/037 |
| | | | 715/771 |
| 2010/0299155 A1 | 11/2010 | Findlay et al. | |
| 2011/0072367 A1 | 3/2011 | Bauer | |
| 2011/0082710 A1* | 4/2011 | Subash | G06Q 10/10 |
| | | | 705/3 |
| 2013/0011819 A1* | 1/2013 | Horseman | A61B 5/6887 |
| | | | 434/257 |
| 2013/0085771 A1* | 4/2013 | Ghanbari | G16H 10/60 |
| | | | 705/2 |
| 2013/0308839 A1* | 11/2013 | Taylor | G06F 19/321 |
| | | | 382/128 |
| 2013/0325493 A1 | 12/2013 | Wong et al. | |
| 2015/0106122 A1* | 4/2015 | Lee | G16H 10/60 |
| | | | 705/3 |
| 2015/0154361 A1* | 6/2015 | Barsoum | G16H 80/00 |
| | | | 705/3 |
| 2019/0217107 A1* | 7/2019 | Kaula | A61N 1/36185 |

OTHER PUBLICATIONS

International Bureau of WIPO, Notification and International Preliminary Report on Patentability for related International Appln. No. PCT/US2017/026148, dated Oct. 18, 2018, 9 pages.

* cited by examiner

Fig. 15

AVATAR-BASED HEALTH PORTAL WITH MULTIPLE NAVIGATIONAL MODES

CROSS REFERENCE TO RELATED APPLICATIONS

This is the National Stage filed under 35 U.S.C. § 371 of International Application PCT/US2017/026148, filed Apr. 5, 2018, which designated the United States of America, the disclosure of which is incorporated herein by reference. This application claims the benefit U.S. Application Ser. No. 62/318,708, filed Apr. 5, 2016, the entire contents of which are hereby incorporated by reference.

BACKGROUND OF THE INVENTION

Recent progress in genomics and other technologies along with the rising importance of age-related diseases have opened an opportunity to revolutionize health and the practice of medicine. For example, the costs of genomic sequencing have decreased by more than four orders of magnitude over the last fifteen years. The same shotgun sequencing techniques Venter, et al. developed to revolutionize human whole-genome sequencing are now also being used to define and explore the microbiome. Sometimes called our "second genome," the microbiome is composed of the trillions of bacteria and other microorganisms that live in and on our body, all with their own genetic material interacting with our own human cells to support health and cause or be associated with disease. Combining human whole-genome sequencing and microbiome characterization with recent progress in measuring metabolomics, the small molecules and chemicals that result from protein synthesis and other basic physiologic functions will provide new opportunities in medical diagnosis, early detection, and prevention.

Similarly dramatic advancements are being made in clinical imaging, and combining imaging with genomics is likely to become increasingly important in medical practice. Magnetic resonance imaging (MRI) avoids harmful radiation and now image resolution has improved to the point that contrast is no longer required for highly sophisticated imaging of the brain and entire body.

To make use of all these data there needs to be an affordable place to securely store, access and analyze. Fortunately, the availability and decreased costs of cloud computing has made it possible to securely store and analyze genomics and phenotype metadata as integrated health records at scale previously unattainable.

SUMMARY OF THE INVENTION

While vast amounts of medical data are available, current computer-based storage and retrieval systems are impersonal, leave patients to navigate complex information without guidance, and fail to offer navigational alternatives. By way of example, many existing electronic medical record (EMR) systems are not designed to be patient-facing and fail to offer convenient, and more importantly, personalized graphic user interfaces (GUIs). By way of further example, available medical data interfaces do not provide multiple navigational modes that allow patients to organize and traverse data in a way that provides clarity, allow conclusions to be drawn, and medical decisions to be made.

The platforms, systems, media, and methods described herein allow patients to connect and identify with medical information by providing a personalized, animated avatar. Moreover, platforms, systems, media, and methods described herein include multiple navigational modes, which allow patients to choose a style of navigation that suits their way of thinking about the information and their goals in viewing the information. These innovations facilitate personal connections to the information, which are easily lost in the modern age of medicine where many interactions are web- and mobile-based.

An aspect of the disclosure provides an interactive health portal for presentation of health information of an individual. The portal personalizes the information and allows the individual to review and organize the information to make it more useful. The health information can be of any type susceptible to electronic display, for example, laboratory test results, survey results, medical imaging results, genomic analysis results, microbiomic analysis results, metabolomic analysis results, and sensor data. In some cases, the health information is broken down into categories of information. In some cases, the categories of health information are further broken down into subcategories of information.

An aspect of the disclosure provides an animated three-dimensional avatar of the individual to whom the health information presented in the portal pertains. The avatar is generated based on the appearance of the individual, which provides customization and personalization to the portal and the health information. Various imaging methodologies are suitable to capture the appearance of the individual and generate the avatar. Generally, the avatar is life-like in appearance and animated. For example, the avatar may stand, sit, walk, talk, sleep, and interact with the user.

An aspect of the disclosure provides optional navigational modes. The navigation modes are used within the interactive health portal to view, browse, traverse, search, sort, filter, display, report the health information of the individual. The number of navigational modes available to the individual varies in different implementations. For example, 1, 2, 3, 4, 5, 6, 7, 8, 9, 10 or more modes may be available to the individual. The individual may have unrestricted access to the navigational modes, or alternatively, an administrator may have the ability to restrict access to one or more of the modes.

An example of a suitable navigational mode is a collage mode displaying a collage of icons representing the subcategories around the display of the avatar. Another example of a suitable navigational mode is a list navigational mode displaying text elements representing the categories and the subcategories, the text elements arranged hierarchically to represent the relationship between the categories and the subcategories. Another example of a suitable navigational mode is a two-dimensional map navigational mode displaying icon elements representing the categories arranged circularly and displaying icon elements representing the subcategories arranged circularly around the icon elements representing the categories to represent the relationship between the categories and the subcategories. Yet another example of a suitable navigational mode is a three-dimensional landscape navigational mode displaying the avatar in a three-dimensional landscape with regions representing the categories and the subcategories; wherein each navigational mode comprises an element to navigate to the display of the avatar.

The navigational modes are suitably operated by the individual via a number of input mechanisms. In some cases, the navigational modes are used via gestures, which are captured by a touchscreen or multi-touchscreen, a camera, a motion sensor, or the like. In some cases, the navigational modes are used via a pointing device such as a mouse, stylus, or the like.

An aspect of the disclosure provides computer-implemented systems comprising: a digital processing device comprising: at least one processor, an operating system configured to perform executable instructions, a memory, and a computer program including instructions executable by the digital processing device to create an interactive health portal for presentation of health information of an individual comprising: a software module providing a display of an animated three-dimensional avatar of the individual, the avatar generated by three-dimensional imaging of the individual's person; and one or more software modules providing at least one of the following distinct navigational modes for navigating a plurality of categories of health information, each category having at least one subcategory of health information, the modes comprising: a list navigational mode displaying text elements representing the categories and the subcategories, the text elements arranged hierarchically to represent the relationship between the categories and the subcategories; a two-dimensional map navigational mode displaying icon elements representing the categories arranged circularly and displaying icon elements representing the subcategories arranged circularly around the icon elements representing the categories to represent the relationship between the categories and the subcategories; and a three-dimensional landscape navigational mode displaying the avatar in a three-dimensional landscape with regions representing the categories and the subcategories; wherein each navigational mode comprises an element to navigate to the display of the avatar, and wherein the individual can switch between the navigational modes.

An additional aspect of the disclosure provides non-transitory computer-readable storage media encoded with a computer program including instructions executable by a processor to create an interactive health portal for presentation of health information of an individual comprising: a software module providing a display of an animated three-dimensional avatar of the individual, the avatar generated by three-dimensional imaging of the individual's person; and one or more software modules providing at least one of the following distinct navigational modes for navigating a plurality of categories of health information, each category having at least one subcategory of health information, the modes comprising: a list navigational mode displaying text elements representing the categories and the subcategories, the text elements arranged hierarchically to represent the relationship between the categories and the subcategories; a two-dimensional map navigational mode displaying icon elements representing the categories arranged circularly and displaying icon elements representing the subcategories arranged circularly around the icon elements representing the categories to represent the relationship between the categories and the subcategories; and a three-dimensional landscape navigational mode displaying the avatar in a three-dimensional landscape with regions representing the categories and the subcategories; wherein each navigational mode comprises an element to navigate to the display of the avatar, and wherein the individual can switch between the navigational modes.

An additional aspect of the disclosure provides computer-implemented methods of providing an interactive health portal for presentation of health information of an individual, the method comprising: displaying, by a computer, an animated three-dimensional avatar of the individual, the avatar generated by three-dimensional imaging of the individual's person; and providing, by the computer, at least one of the following distinct navigational modes for navigating a plurality of categories of health information, each category having at least one subcategory of health information, the modes comprising: a list navigational mode displaying text elements representing the categories and the subcategories, the text elements arranged hierarchically to represent the relationship between the categories and the subcategories; a two-dimensional map navigational mode displaying icon elements representing the categories arranged circularly and displaying icon elements representing the subcategories arranged circularly around the icon elements representing the categories to represent the relationship between the categories and the subcategories; and a three-dimensional landscape navigational mode displaying the avatar in a three-dimensional landscape with regions representing the categories and the subcategories; wherein each navigational mode comprises an element to navigate to the display of the avatar, and wherein the individual can switch between the navigational modes.

All medical information appearing in this document is fictitious and is not associated with any real person.

BRIEF DESCRIPTION OF THE DRAWINGS

A better understanding of the features and advantages of the present subject matter will be obtained by reference to the following detailed description that sets forth illustrative embodiments and the accompanying drawings of which:

FIG. 15 shows a non-limiting example of a subcategory of health information; in this case, a summary of survey data pertaining to tobacco use;

DETAILED DESCRIPTION OF THE INVENTION

Figure 1:
FIG. 1 shows a non-limiting example of an interface for using a navigational mode; in this case, an interface for using a collage navigational mode.

Included within this disclosure are computer-implemented systems comprising: a digital processing device comprising: at least one processor, an operating system configured to perform executable instructions, a memory, and a computer program including instructions executable by the digital processing device to create an interactive health portal for presentation of health information of an individual comprising: a software module providing a display of an animated three-dimensional avatar of the individual, the avatar generated by three-dimensional imaging of the individual's person; and one or more software modules providing at least one of the following distinct navigational modes for navigating a plurality of categories of health information, each category having at least one subcategory of health information, the modes comprising: a list navigational mode displaying text elements representing the categories and the subcategories, the text elements arranged hierarchically to represent the relationship between the categories and the subcategories; a two-dimensional map navigational mode displaying icon elements representing the categories arranged circularly and displaying icon elements representing the subcategories arranged circularly around the icon elements representing the categories to represent the relationship between the categories and the subcategories; and a three-dimensional landscape navigational mode displaying the avatar in a three-dimensional landscape with regions representing the categories and the subcategories; wherein each navigational mode comprises an element to navigate to the display of the avatar, and wherein the individual can switch between the navigational modes.

Also included within this disclosure are non-transitory computer-readable storage media encoded with a computer program including instructions executable by a processor to create an interactive health portal for presentation of health information of an individual comprising: a software module providing a display of an animated three-dimensional avatar of the individual, the avatar generated by three-dimensional imaging of the individual's person; and one or more software modules providing at least one of the following distinct navigational modes for navigating a plurality of categories of health information, each category having at least one subcategory of health information, the modes comprising: a list navigational mode displaying text elements representing the categories and the subcategories, the text elements arranged hierarchically to represent the relationship between the categories and the subcategories; a two-dimensional map navigational mode displaying icon elements representing the categories arranged circularly and displaying icon elements representing the subcategories arranged circularly around the icon elements representing the categories to represent the relationship between the categories and the subcategories; and a three-dimensional landscape navigational mode displaying the avatar in a three-dimensional landscape with regions representing the categories and the subcategories; wherein each navigational mode comprises an element to navigate to the display of the avatar, and wherein the individual can switch between the navigational modes.

Also included within this disclosure are computer-implemented methods of providing an interactive health portal for presentation of health information of an individual, the method comprising: displaying, by a computer, an animated three-dimensional avatar of the individual, the avatar generated by three-dimensional imaging of the individual's person; and providing, by the computer, at least one of the following distinct navigational modes for navigating a plurality of categories of health information, each category having at least one subcategory of health information, the modes comprising: a list navigational mode displaying text elements representing the categories and the subcategories, the text elements arranged hierarchically to represent the relationship between the categories and the subcategories; a two-dimensional map navigational mode displaying icon elements representing the categories arranged circularly and displaying icon elements representing the subcategories arranged circularly around the icon elements representing the categories to represent the relationship between the categories and the subcategories; and a three-dimensional landscape navigational mode displaying the avatar in a three-dimensional landscape with regions representing the categories and the subcategories; wherein each navigational mode comprises an element to navigate to the display of the avatar, and wherein the individual can switch between the navigational modes.

Certain Definitions

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

Animated Three-Dimensional Avatar

The platforms, systems, media, and methods described herein include an animated three-dimensional avatar, or use of the same. To effectuate this, the platforms, systems, media, and methods described herein include a software module providing a display of a three-dimensional avatar of the individual (e.g., patient) to whom the health information pertains. The avatar described herein displays the physical characteristics of the individual including, by way of examples, height, weight, eye color, skin color, hair length, style, pattern, and color, facial structure, bone structure, and the like. The avatar may have an audio presence which reflects the voice of the individual.

An avatar of the individual, in some cases, personalizes the interface and creates a personal connection to the medial information presented. Navigational elements may be displayed in proximity to, and in relation to, the avatar. Interacting with the avatar, in some cases, provides access to various categories of health information, in other words, the avatar acts as a navigational element. By way of example, interacting with the specific aspects of avatar provides access to relevant categories of health information, for example, interacting with the chest of the avatar provides access to echocardiogram information, interacting with the head of the avatar provides access to brain MRI information, and interacting with the abdomen of the avatar provides access to microbiome information, etc.

Many methods for generating the avatar are suitable. For example, the avatar may be generated by three-dimensional imaging of the individual's person. Many three-dimensional imaging methodologies are suitable. By way of example, the three-dimensional imaging may be performed using an array of cameras to image the individual from a plurality of angles simultaneously. Such cameras may be arranged in a spherical, hemi-spherical, circular, or semi-circular pattern around the individual during the imaging. A suitable array of cameras includes, for example, 5, 10, 20, 30, 40, 50, 60, 70, 80, 90, 100, 200, 300, 400, 500 or more cameras, including increments therein. The three-dimensional imaging may comprise capturing one or more photographs of the individual and/or capturing one or more videos of the individual. The cameras are optionally high-definition cameras and the photographs and/or videos are optionally high-definition media.

The avatar may be animated to create a sense that it represents the individual and to signal that it is interactive. Animation, in some cases, imparts a lifelike character to the avatar. Many types of animation are suitable. For example, the photographs and/or videos captured of the individual may be used to programmatically create the animation. Animation suitably simulates a wide variety of activities. By way of non-limiting examples, suitable animation simulates daily activities like standing, walking, talking, sitting, sleeping, eating, driving, and reading. By way of further non-limiting examples, suitable animation simulates sporting activities like running, jumping, cycling, swimming, rowing, weight lifting, and engaging in various individual and team sports. By way of still further non-limiting examples, suitable animation simulates various moods and health statuses of the individual.

Additional avatars are optionally provided that share the physical characteristics of family members of the individual. By way of examples, avatars are optionally provided that resemble the individual's spouse, parents, grandparents, children, and/or grandchildren. Where health information is available for family members, interacting with these additional avatars may provide access to health information for the family members of the individual. In such cases, the avatars act as navigational elements allowing the user to switch the active set of health information. In a particular example, a "family portrait" of avatars provides a GUI to optionally access the health information for all the members of a family.

Referring to FIG. 1, in a particular embodiment, an interactive health portal includes an animated three-dimensional avatar 100 of the individual to whom the health information pertains. In this case, the animated three-dimensional avatar is shown standing in the center of the GUI and the navigational elements of a collage navigational mode are presented around the avatar.

Navigational Modes

The platforms, systems, media, and methods described herein include one or more navigational modes, or use of the same. The interactive health portal for presentation of health information of an individual described herein may offer users 1, 2, 3, 4, 5, 6, 7, 8, 9, 10 or more navigational modes. One or more of the navigational modes are optionally selected from: a collage navigational mode, a list navigational mode, a two-dimensional map navigational mode, and a three-dimensional landscape navigational mode.

A navigational mode includes the set of GUI elements that a user employs to browse, navigate, and access health information and the programming logic that dictates whether such elements are active, how such elements appear, and how such elements function. In some cases, a navigational mode also includes tools and features that a user has the option to employ to view, traverse, track, display, and report their health information within the interactive health portal.

Collage Navigational Mode

The platforms, systems, media, and methods described herein may include a collage navigational mode, or use of the same. In a collage navigational mode, a collage of icons, labels, or other navigational elements, representing categories and/or subcategories of health information, are displayed around the avatar or a navigational element providing access to the avatar. The organization of the navigational elements about the avatar is optionally driven by, for example, amount of data, quality of data, creation date of the data, and/or importance of the data to the individual.

Referring again to FIG. 1, in a particular embodiment, a three-dimensional, animated avatar 100 is surrounded by icons and labels allowing access to: DXA bone mineral density information 101, birthplace information 102, microbiome information 103, gait and balance information 104, Mill brain segmentation information 105, eye color information 106, height information 107, genome information 108, echocardiogram information 109, cognitive capacity information 110, sensory trait information 111, ancestry information 112, whole body MRI information 113, birthday information 114, and pharmacogenomic information 115.

List Navigational Mode

The platforms, systems, media, and methods described herein may include a list navigational mode, or use of the same. In a list navigational mode, text and/or graphic elements representing categories and subcategories of health information are arranged hierarchically to represent the relationship between the categories and the subcategories.

Figure 2:
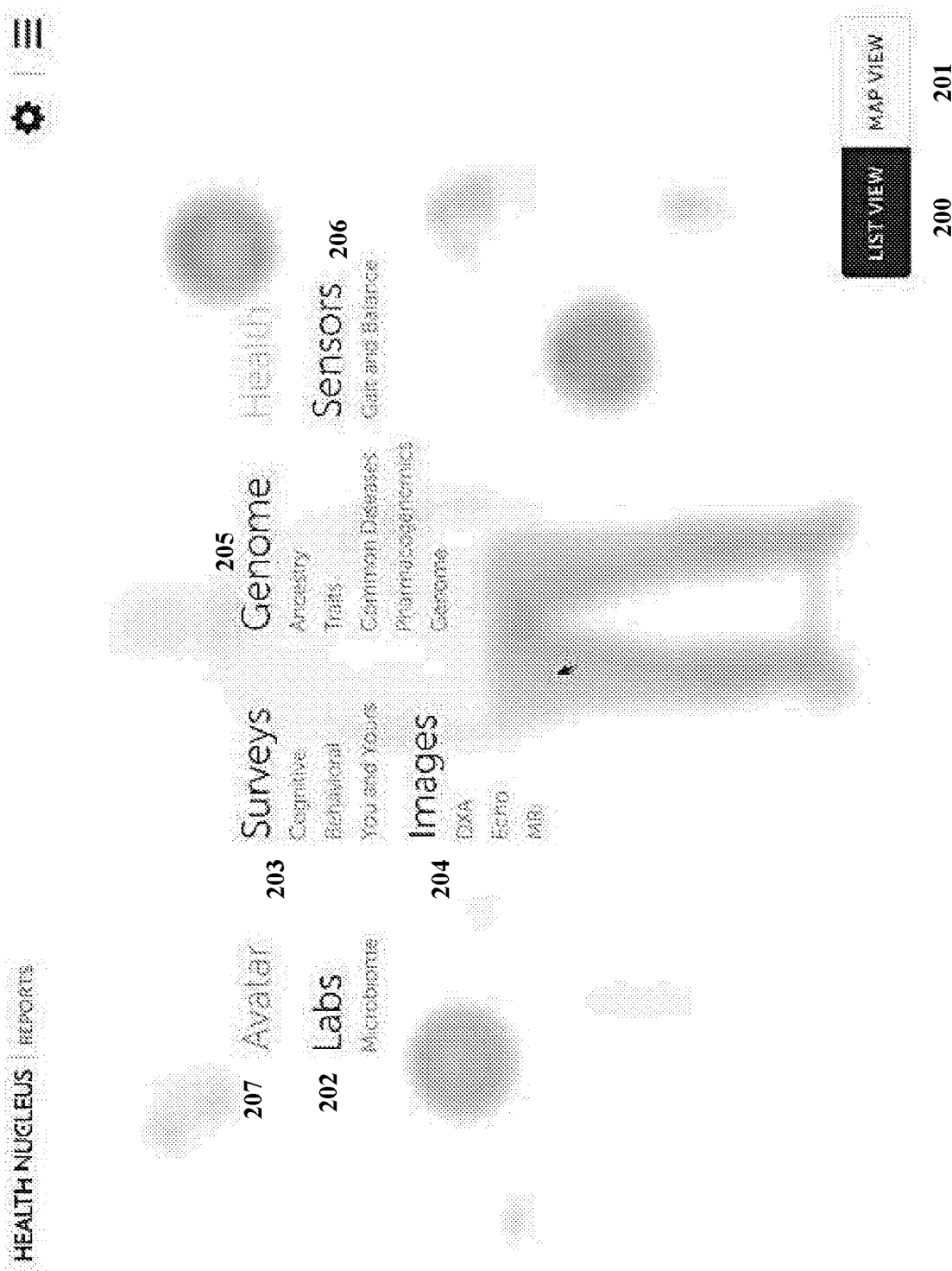
FIG. 2 shows a non-limiting example of an interface for using a navigational mode; in this case, an interface for using a list navigational mode.

Referring to FIG. 2, in a particular embodiment, text navigational elements are provided in a hierarchical display. The hierarchical display is optionally viewable in a list view and in a map view and interface elements are provided that allow a user to toggle between the list view 200 and the map view 201. This embodiment is shown in list view 200. A labs category 202 includes microbiome information. A survey category 203 includes cognitive and behavioral information for the individual and their family members. An images category 204 includes DXA, echo, and MRI information. A genome category 205 includes ancestry, trait, disease, pharmacogenomic, and genome information. And, a sensors category 206 includes gait and balance information. In this embodiment, a link to the three-dimensional, animated avatar display 207 is also included.

Two-Dimensional Map Navigational Mode

The platforms, systems, media, and methods described herein may include a two-dimensional map navigational mode, or use of the same. A two-dimensional map navigational mode includes icons, text elements, or other navigational elements representing categories of health information arranged circularly around the avatar or a navigational element providing access to the avatar. The organization of the navigational elements is optionally driven by, for example, amount of data, quality of data, creation date of the data, and/or importance of the data to the individual. A two-dimensional map navigational mode optionally includes icons, text elements, or other navigational elements representing subcategories of health information arranged circularly around each element representing a category of health information. In such cases, the elements representing the subcategories of health information are arranged around the elements representing the categories of health information to represent the relationship between the categories and the subcategories. Again, the organization of the navigational elements is optionally driven by, for example, amount of data, quality of data, creation date of the data, and/or importance of the data to the individual.

Figure 3:
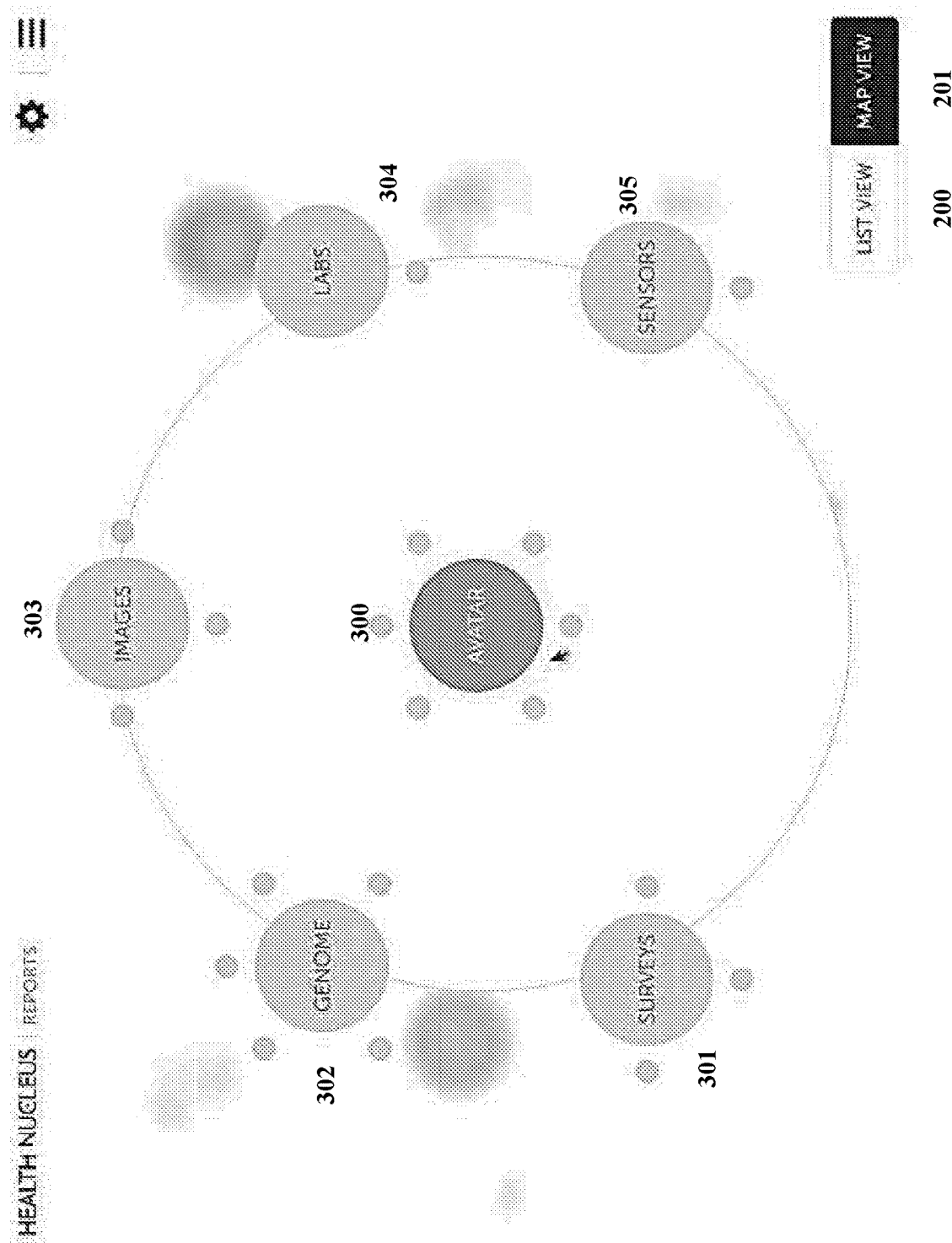
FIG. 3 shows a non-limiting example of an interface for using a navigational mode; in this case, an interface for using a two-dimensional map navigational mode.

Referring to FIG. 3, in a particular embodiment, text navigational elements are provided in a hierarchical display. The hierarchical display is optionally viewable in a list view and in a map view and interface elements are provided that allow a user to toggle between the list view 200 and the map view 201. This embodiment is shown in map view 201. In this case, five navigational elements providing access to categories of health information are arranged circularly around a navigational element providing access to the three-dimensional, animated avatar 300. In this embodiment, the categories are surveys 301, genome 302, images 303, labs 304, and sensors 305.

Three-Dimensional Landscape Navigational Mode

The platforms, systems, media, and methods described herein may include a three-dimensional landscape navigational mode, or use of the same. In a three-dimensional landscape navigational mode, the avatar is displayed in a three-dimensional landscape with regions representing categories of health information. Each category of health information is optionally depicted to indicate associated subcategories of health information. Further, in a three-dimensional landscape navigational mode, the avatar is shown traveling to a region in order to indicate the current category and/or subcategory of health information accessed.

Figure 4A:
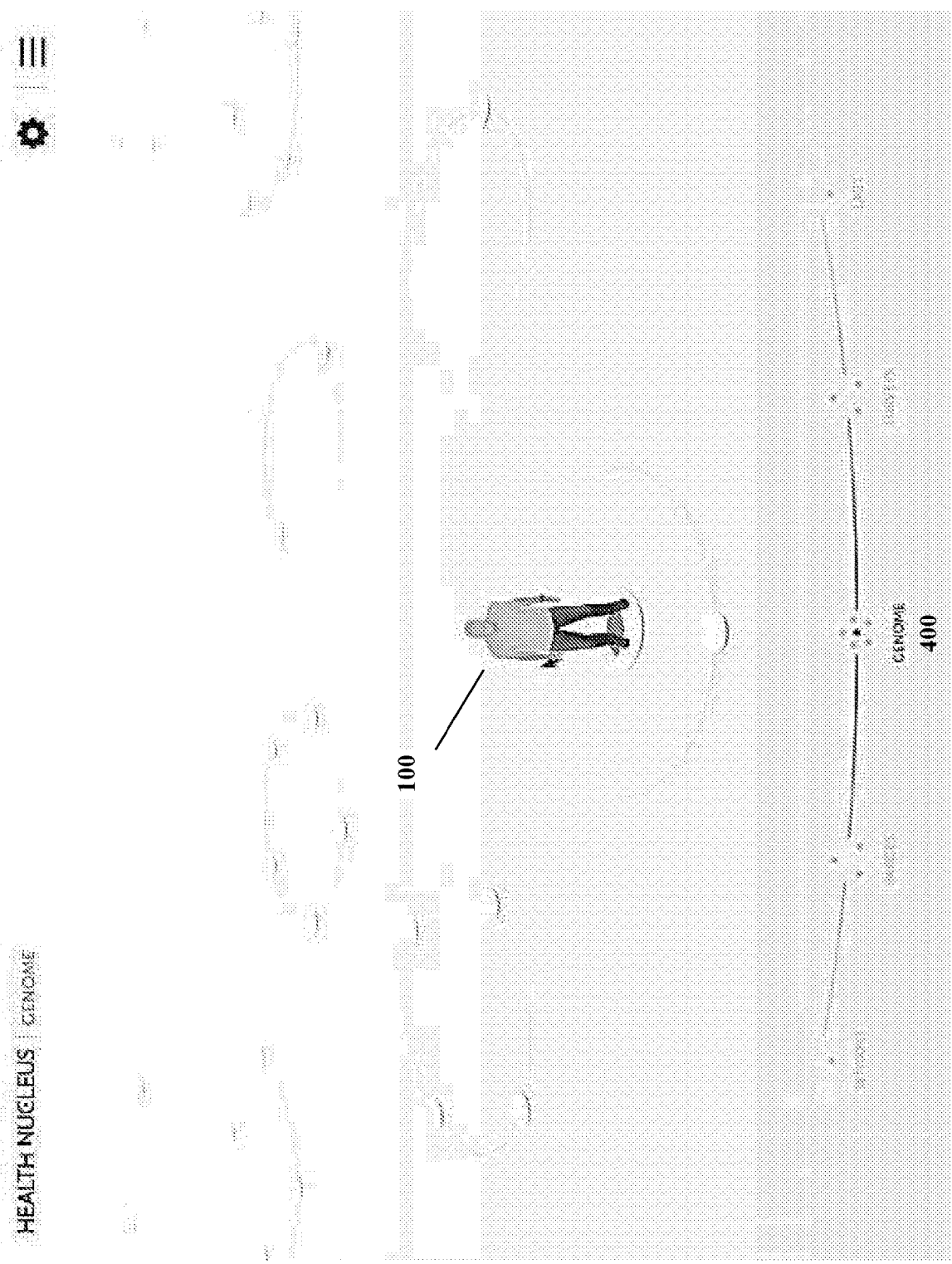
FIG. 4A shows a non-limiting example of an interface for using a navigational mode; in this case, an interface for using a three-dimensional landscape navigational mode (zoomed out to show overview of health information)

Referring to FIG. 4A, in a particular embodiment, a three-dimensional, animated avatar of the individual 100 is depicted in a genome region 400 allowing the individual to access subcategories of genome information.

Figure 4B:
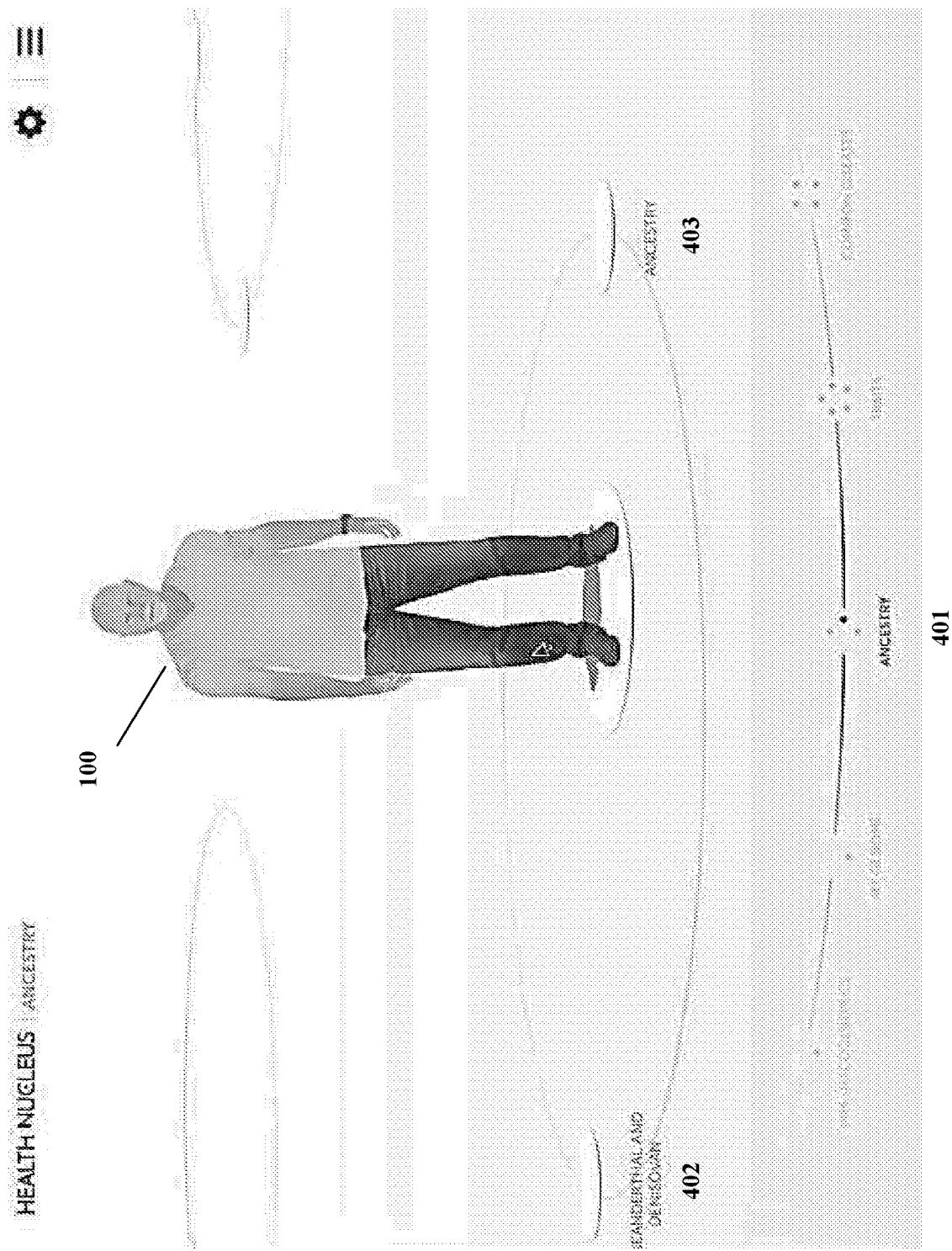
FIG. 4B shows a non-limiting example of an interface for using a navigational mode; in this case, an interface for using a three-dimensional landscape navigational mode (zoomed in to show detail of health information)

Referring to FIG. 4B, in a particular embodiment, a three-dimensional, animated avatar of the individual 100 is depicted in an ancestry region 401 allowing the individual to access still further subcategories of ancestry information. In this case, the subcategories of ancestry information include Neanderthal and Denisovan composition 402 and maternal and paternal ancestry maps 403.

Navigational Mode Switching

The platforms, systems, media, and methods described herein may allow a user to switch between navigational modes. The individual user (e.g., patient) optionally switches between navigational modes by interacting with GUI elements to indicate their current navigational preference. The different navigational modes allow the individual to view, traverse, and browse health information using varying methodologies and modes of user input based on the preference of the individual, the type of information, and the individual's health and informational goals. In some cases, the individual optionally switches between navigational modes at will. In other cases, the individual user (e.g., patient) is restricted to one or more navigational modes by an administrator or restricted with regard to when one or more navigational modes are available.

Categories of Health Information

The platforms, systems, media, and methods described herein include health information, or use of the same. The health information may be organized into a plurality of categories of information. For example, the platforms, systems, media, and methods described herein suitably include 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100 or more categories of health information, including increments therein. Each category of health information may also be further organized into at least one subcategory of health information; thus, forming a hierarchy of health information. For example, each category of health information suitably includes 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100 or more subcategories of health information, including increments therein. As such, the hierarchy of health information suitably includes many levels, such as simple 1, 2, and 3 layer hierarchies as well as complex 5, 10, or 20 layer hierarchies of health information, including intermediate levels of complexity.

Each category of health information may comprise a health report resulting from a battery of medical tests, procedures, and measurements. In some cases, the categories of health information are accessible by interacting with the avatar and/or with navigational elements presented as part of one or more navigational modes.

Categories of health information are optionally organized by relevant part of the body. By way of example, categories of health information may include, brain, head, chest (e.g., heart and/or lungs), right arm, left arm, stomach, pelvis, right leg, left leg, and whole body. In some cases, for a brain category, subcategories of health information include cognitive, gait and balance, and MRI information. In some cases, for a head category, subcategories of health information include vision, hearing, breathing, and facial analysis information. In some cases, for a heart category, subcategories of health information include metabolite, echo, ECG, and rhythm information. In some cases, for a lungs category, subcategories of health information include MRI and behavioral (e.g., smoking) information. In some cases, for an arm category, subcategories of health information include DXA information, such as fat mass, lean mass, and bone density information. In some cases, for a stomach category, subcategories of health information include microbiome, visceral adipose tissue, food sensitivity, metabolite, and metabolomic information. In some cases, for a pelvis category, subcategories of health information include, for males, prostate, reproductive organ, and hormonal information and for females, cervix, reproductive organ, and hormonal information. In some cases, for a leg category, subcategories of health information include dual energy x-ray absorptiometry (DXA) information, such as fat mass, lean mass, and bone density. In some cases, for a whole body category, subcategories of health information include BMI, muscle-to-fat ratio, bone density, resting metabolic rate, medical history, family medical history, and behavioral health information.

Figure 5:
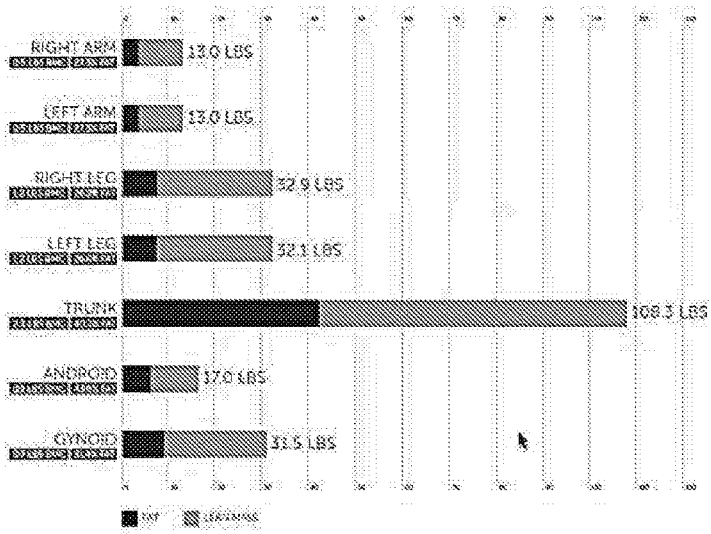
FIG. 5 shows a non-limiting example of a subcategory of health information; in this case, a summary of body composition data.
Figure 5:
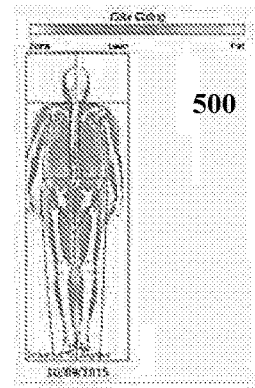
Figure 5:

Referring to FIG. 5, in a particular embodiment, DXA body composition health information is provided. An overview of body composition is provided that includes a composition heat map 500. Additionally, body composition is provided for each major body region 501 including right arm, left arm, right leg, left leg, trunk, as well as android and gynoid regions. Finally, a World Health Organization (WHO) BMI classification 502 is provided for the individual.

Figure 6:
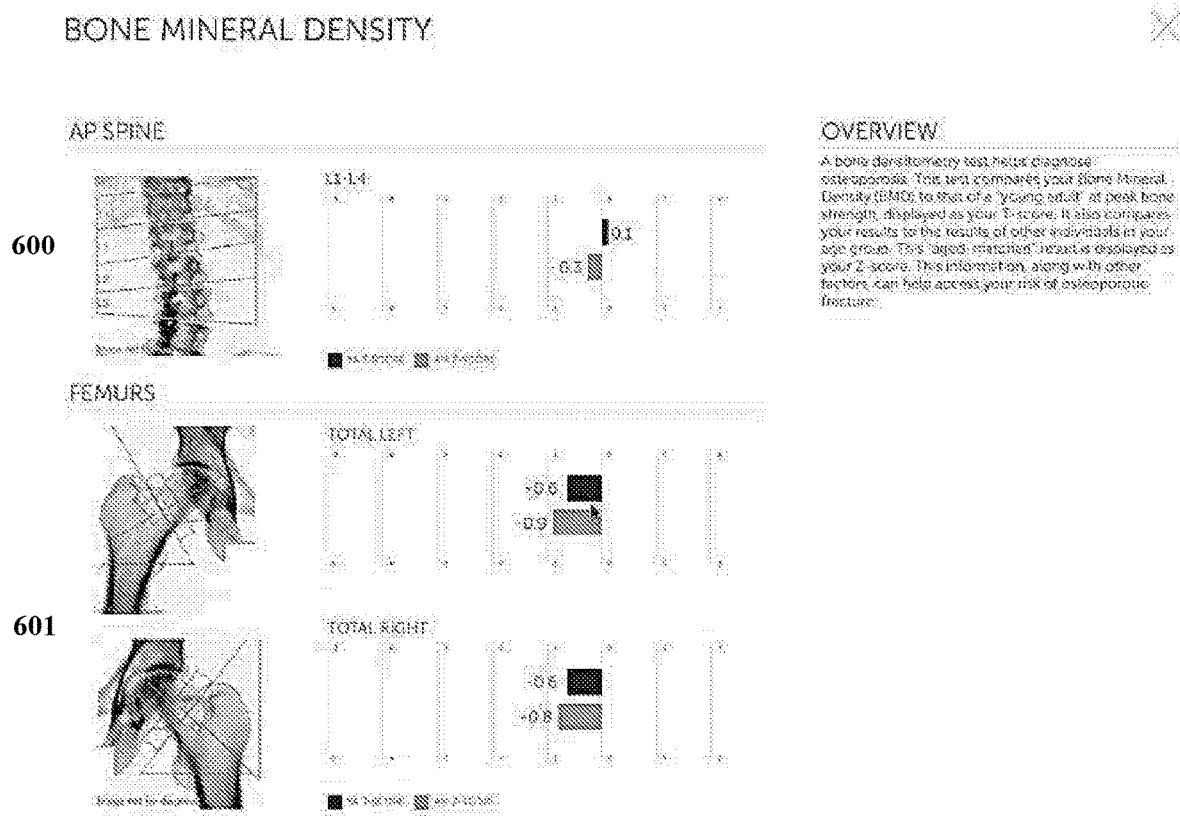
FIG. 6 shows a non-limiting example of a subcategory of health information; in this case, a summary of bone mineral density data.

Referring to FIG. 6, in a particular embodiment, bone mineral density health information is provided. An overview of bone densitometry is provided. Additionally, bone density is provided for the spine 600 and the heads of the femurs 601.

Categories of health information are also optionally organized by genomics. By way of example, categories of health information may include genetic health traits, rare (Mendelian) disease variations, ancestry, common disease risk, inherited cancer, pharmacogenomics, and carrier status. In some cases, for a genetic health traits category, subcategories of health information include blood group, food allergies, food preference, taste sensitivity, macro-nutrient metabolism, vitamin and mineral metabolism, chemical and environmental allergies, insect and pathogen exposure and sensitivity, and sensory and emotional exposure information. In some cases, for a rare (Mendelian) disease variations category, subcategories of health information include chromosome, position, amino acid change, genotype, disease, gene, and mode of inheritance information. In some cases, for an ancestry category, subcategories of health information include Y chromosome ancestry, mitochondrial DNA ancestry, and ethnicity information. In some cases, for a common disease risk category, subcategories of health information include coronary artery disease, Alzheimer's disease, diabetes, hypertension, blood lipids, osteoarthritis, Parkinson's disease, and rheumatoid arthritis information. In some cases, for an inherited cancer category, subcategories of health information include chromosome, position, amino acid change, genotype, disease, gene, and mode of inheritance information. In some cases, for a pharmacogenomics category, subcategories of health information include chromosome, position, amino acid change, genotype, disease, gene, and mode of inheritance information. In some cases, for a carrier status category, subcategories of health information include chromosome, position, amino acid change, genotype, disease, gene, and mode of inheritance information, for both pathogenic and likely pathogenic variants. In a particular case, genomic information is presented on a genome wall map.

Figure 7A:
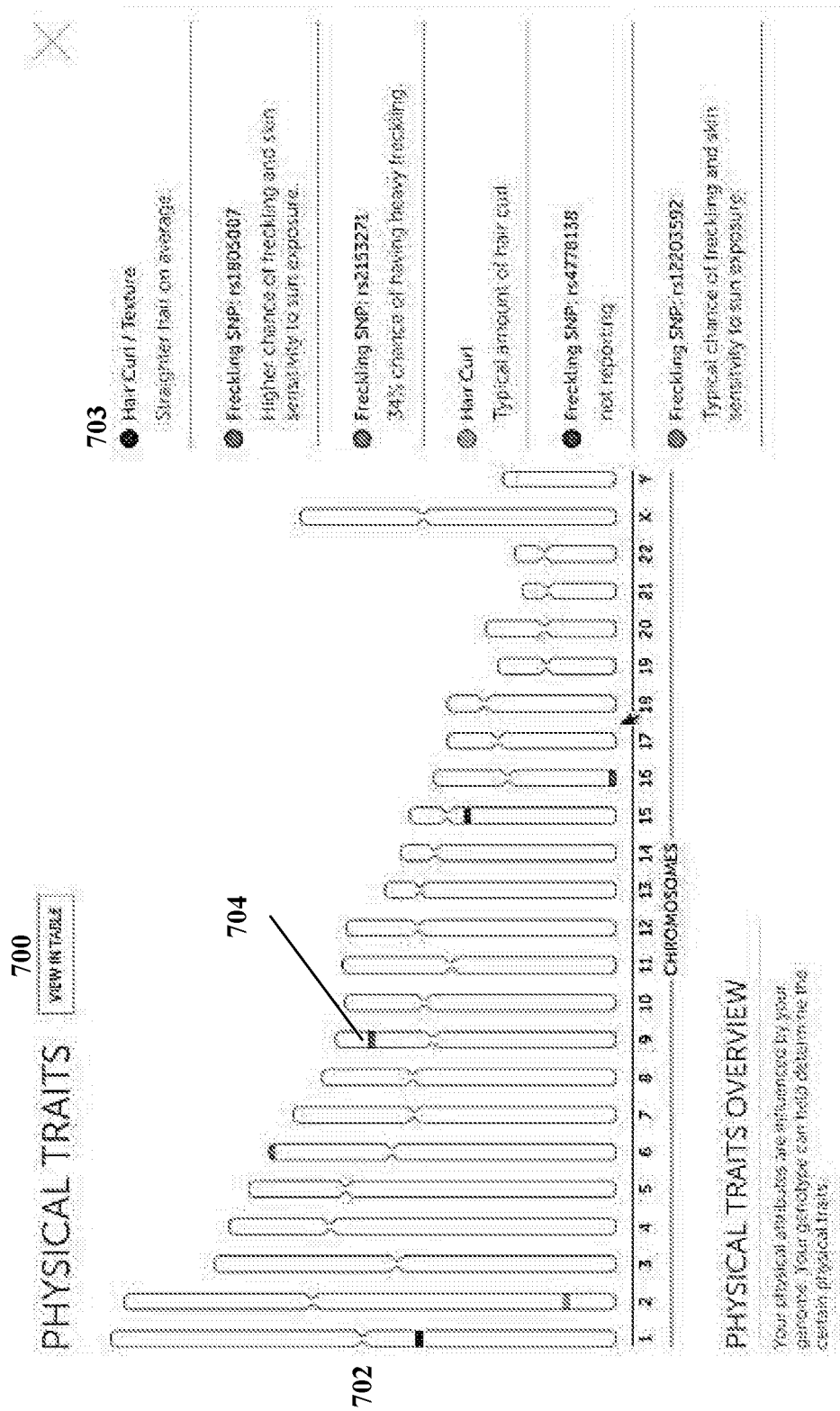
FIG. 7A shows a non-limiting example of a subcategory of health information; in this case, a summary of physical traits, including associated SNPs and genotypes, in chart form.

Referring to FIG. 7A, in a particular embodiment, physical trait health information is provided. The physical trait health information is optionally viewable in a chart view and in a table view and interface elements are provided that allow a user to toggle between the table view 700 and the chart view. This embodiment is shown in chart view. A schematic representation of the individual's chromosomes is provided 702, wherein identified SNPs influencing physical traits are listed 703 and depicted on the appropriate region of the appropriate chromosome in the schematic representation 704. In this case, SNPs influencing hair curl/texture as well as freckling are indicated.

Figure 7B:
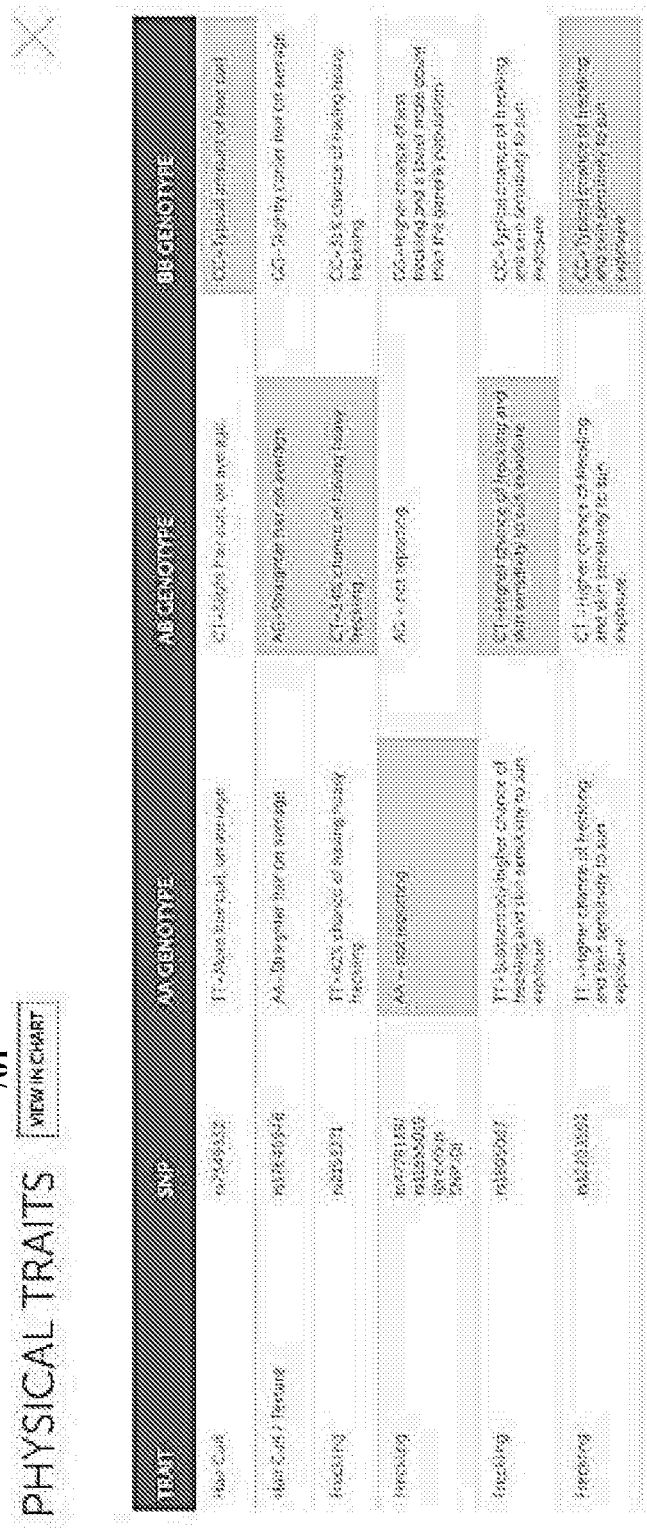
FIG. 7B shows a non-limiting example of a subcategory of health information; in this case, a summary of physical traits, including associated SNPs and genotypes, in table form.

Referring to FIG. 7B, in a particular embodiment, physical trait health information is provided. The physical trait health information is optionally viewable in a chart view and in a table view and interface elements are provided that allow a user to toggle between the table view and the chart view 701. This embodiment is shown in table view. The SNPs of FIG. 7A are depicted in a table and zygosity is indicated.

Figure 8A:
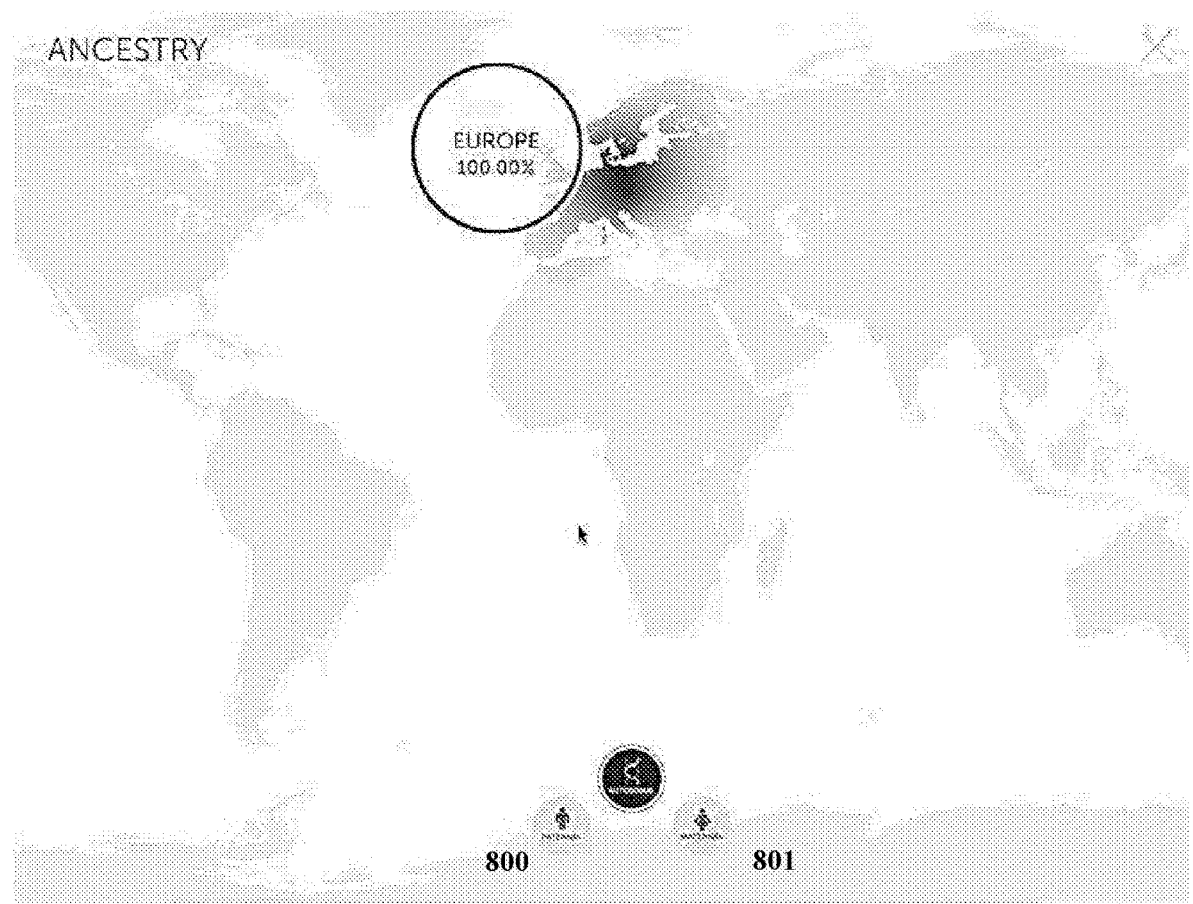
FIG. 8A shows a non-limiting example of a subcategory of health information; in this case, a map of paternal ancestry.

Referring to FIG. 8A, in a particular embodiment, ancestry health information is provided in the form of an ancestral map. The ancestry health information is optionally viewable in a paternal ancestry view and in a maternal ancestry view and interface elements are provided that allow a user to toggle between the paternal ancestry view 800 and the maternal ancestry view 801. This embodiment is shown in paternal ancestry view. In this case, the individual's paternal ancestry is 100% European.

Figure 8B:
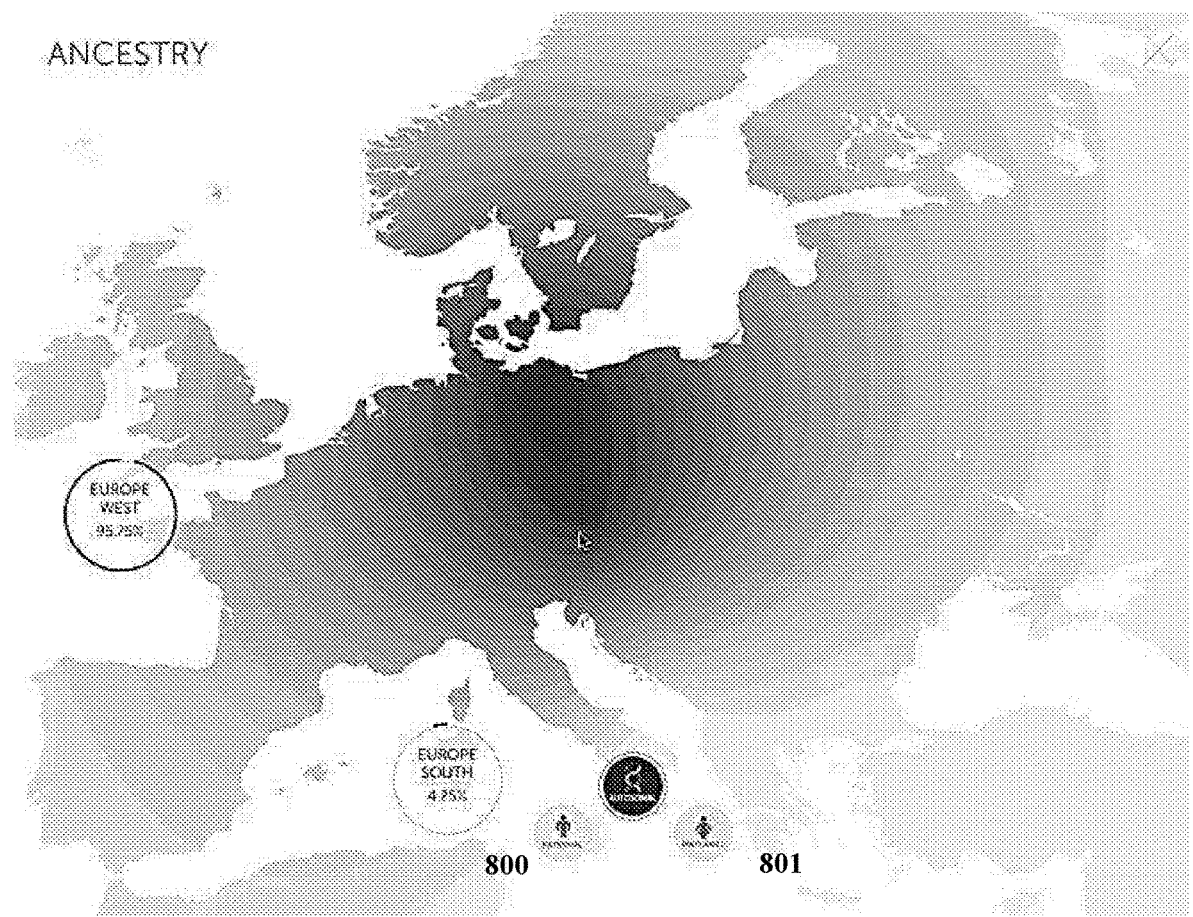
FIG. 8B shows a non-limiting example of a subcategory of health information; in this case, a map of maternal ancestry.

Referring to FIG. 8B, in a particular embodiment, ancestry health information is provided in the form of an ancestral map. The ancestry health information is optionally viewable in a paternal ancestry view and in a maternal ancestry view and interface elements are provided that allow a user to toggle between the paternal ancestry view 800 and the maternal ancestry view 801. This embodiment is shown in maternal ancestry view. In this case, the individual's maternal ancestry is 95.75% Western European and 4.25% Southern European.

Figure 9:
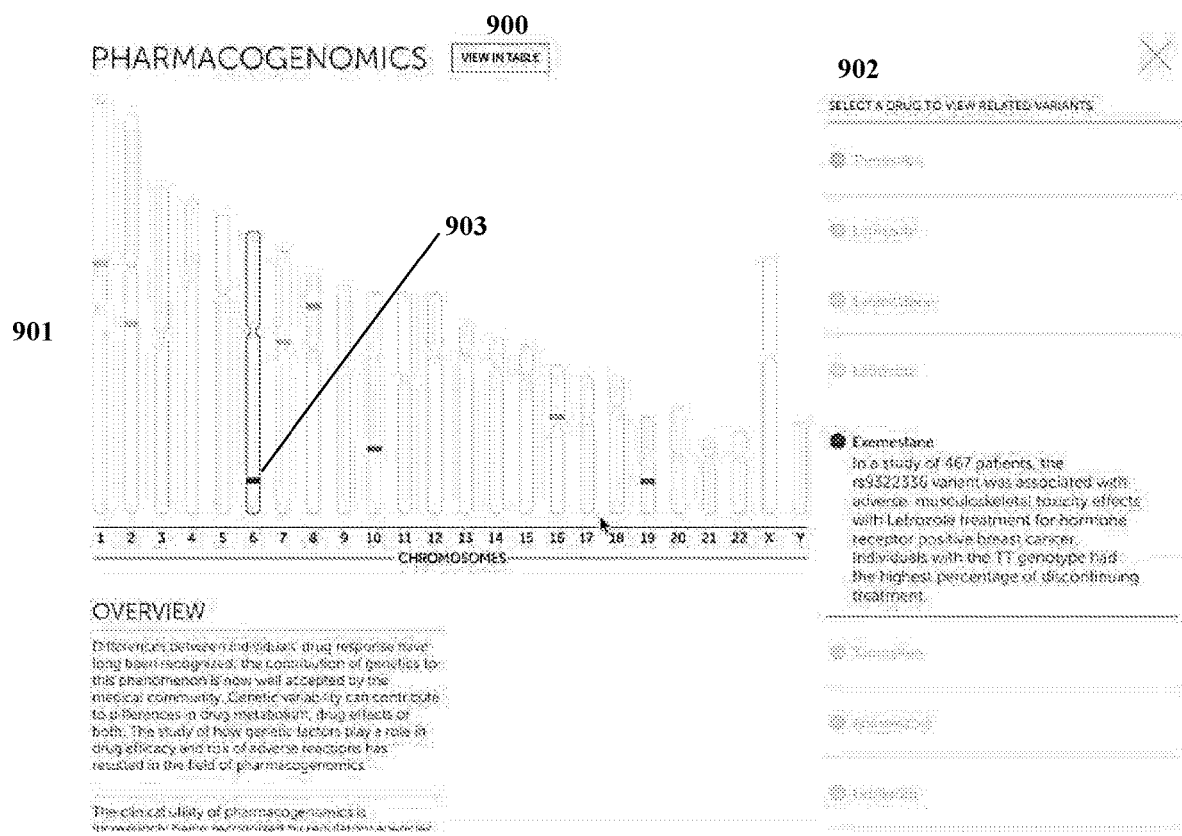
FIG. 9 shows a non-limiting example of a subcategory of health information; in this case, a summary of pharmacogenomics, including associated variants and drug information, in chart form.

Referring to FIG. 9, in a particular embodiment, pharmacogenomic health information is provided. The pharmacogenomic health information is optionally viewable in a chart view and in a table view and interface elements are provided that allow a user to toggle between the table view 700 and the chart view. This embodiment is shown in chart view. A schematic representation of the individual's chromosomes is provided 901, wherein identified SNPs influencing response to specific drugs are listed 902 and depicted on the appropriate region of the appropriate chromosome in the schematic representation 903. In this case, SNPs influencing responses to a number of drugs including exemestane are indicated.

Figure 10:
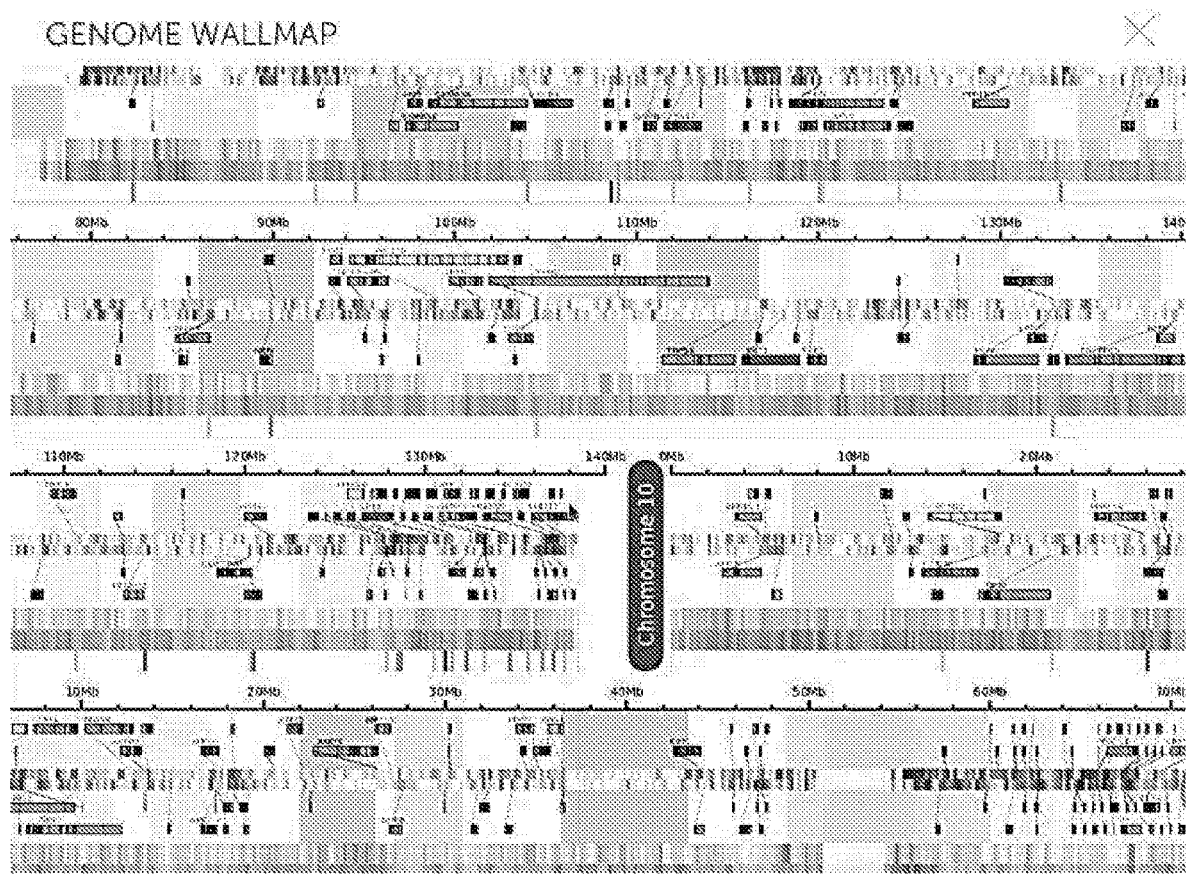
FIG. 10 shows a non-limiting example of a subcategory of health information; in this case, a portion of a genome wall map.

Referring to FIG. 10, in a particular embodiment, genomic health information is provided in the form of a genome wall map. In this case, a genome wall map summarizes all available genomic health information for the individual.

The categories of health information may include, by way of example, a health (disease) category. In some cases, for a disease category, subcategories of health information include neurology, cardiovascular, pulmonary, gastroenterology, nephrology, gynecology, allergy/immunology, rheumatology, dermatology, hematology, oncology, and infectious disease information.

Categories of health information are also optionally organized by phenotype tests. For example, categories of health information may include whole body MRI, brain MRI, cognitive testing, gait and balance testing, DXA testing, echocardiogram, electrocardiogram, heart rhythm monitoring, metabolomics testing, CIMT testing, apnea testing, microbiome testing, behavioral health testing, family medical history, and past medical history. In some cases, for a whole body MRI category, subcategories of health information include differential water uptake for cancer detection (neck, chest, abdomen, pelvis, and whole body) information. In some cases, for a brain MRI category, subcategories of health information include NeuroQuant, anatomy, and diffusion imaging (cancer detection) information. In some cases, for a cognitive category, subcategories of health information include executive function, working memory, and perception information. In some cases, for a gait and balance category, subcategories of health information include fall risk, proprioception, and coordination information. In some cases, for a DXA category, subcategories of health information include bone mineral density, T-score, Z-score, fracture risk, BMI, muscle-to-fat ratio, and age comparison information. In some cases, for an echocardiogram category, subcategories of health information include ejection fraction, z-score aortic root, wall thickness, valve structures, and systolic vs. diastolic function information. In some cases, for an electrocardiogram category, subcategories of health information include evidence of damage, electrical function, rate rhythm, position/axis, chamber size estimate, and rate information. In some cases, for a heart rhythm category, subcategories of health information include arrhythmia, palpitation feedback, anxiety level, and QT segment information. In some cases, for a metabolomics category, subcategories of health information include metabolic capacity of fats, metabolic capacity of protein, metabolic capacity of carbohydrates, and hormonal balance information. In some cases, for a CIMT category, subcategories of health information include flow reduction, stenosis, and risk stratification information. In some cases, for an apnea category, subcategories of health information include number of episodes, correlates, and sleep study information. In some cases, for a microbiome category, subcategories of health information include taxonomy (e.g., kingdom, phylum, genus, and species), genome (e.g., eukaryotes, bacteria, and viruses), resistome (e.g., heat map of antibiotic resistance vs. species), pathogens (e.g., eukaryotes, bacteria, and viruses), and microbial metabolism (e.g., heat map of metabolic pathway vs. species) information. In some cases, for a behavioral category, subcategories of health information include smoking or other tobacco use, alcohol, sleep, anxiety, and depression information. In some cases, for a family medical history category, subcategories of health information include risk reference report and pedigree information. In some cases, for a past medical history category, subcategories of health information include surgery, major illness, vaccination, and medication information.

Figure 11:
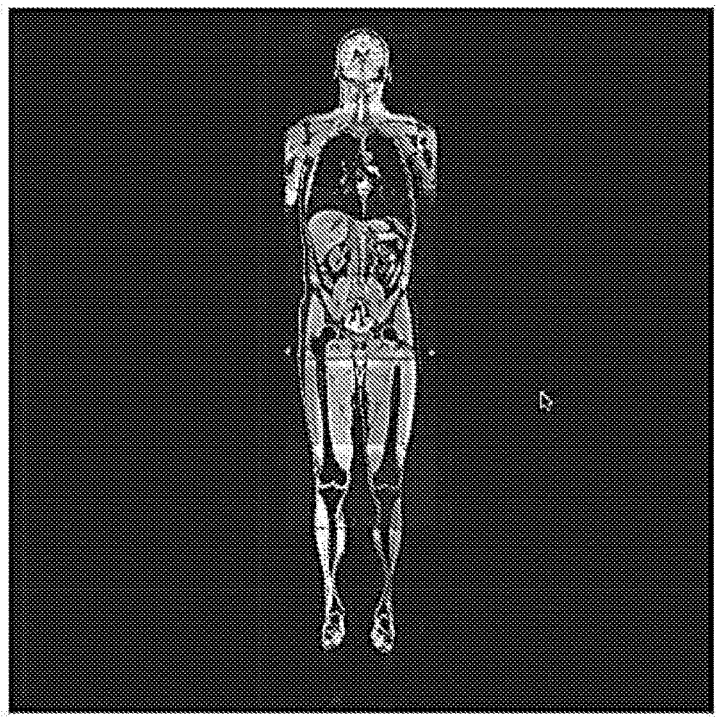
FIG. 11 shows a non-limiting example of a subcategory of health information; in this case, an overview of whole body MRI data.

Referring to FIG. 11, in a particular embodiment, whole body MRI health information is provided. In this case, an overview is provided and whole body MRI images are viewable.

Figure 12:
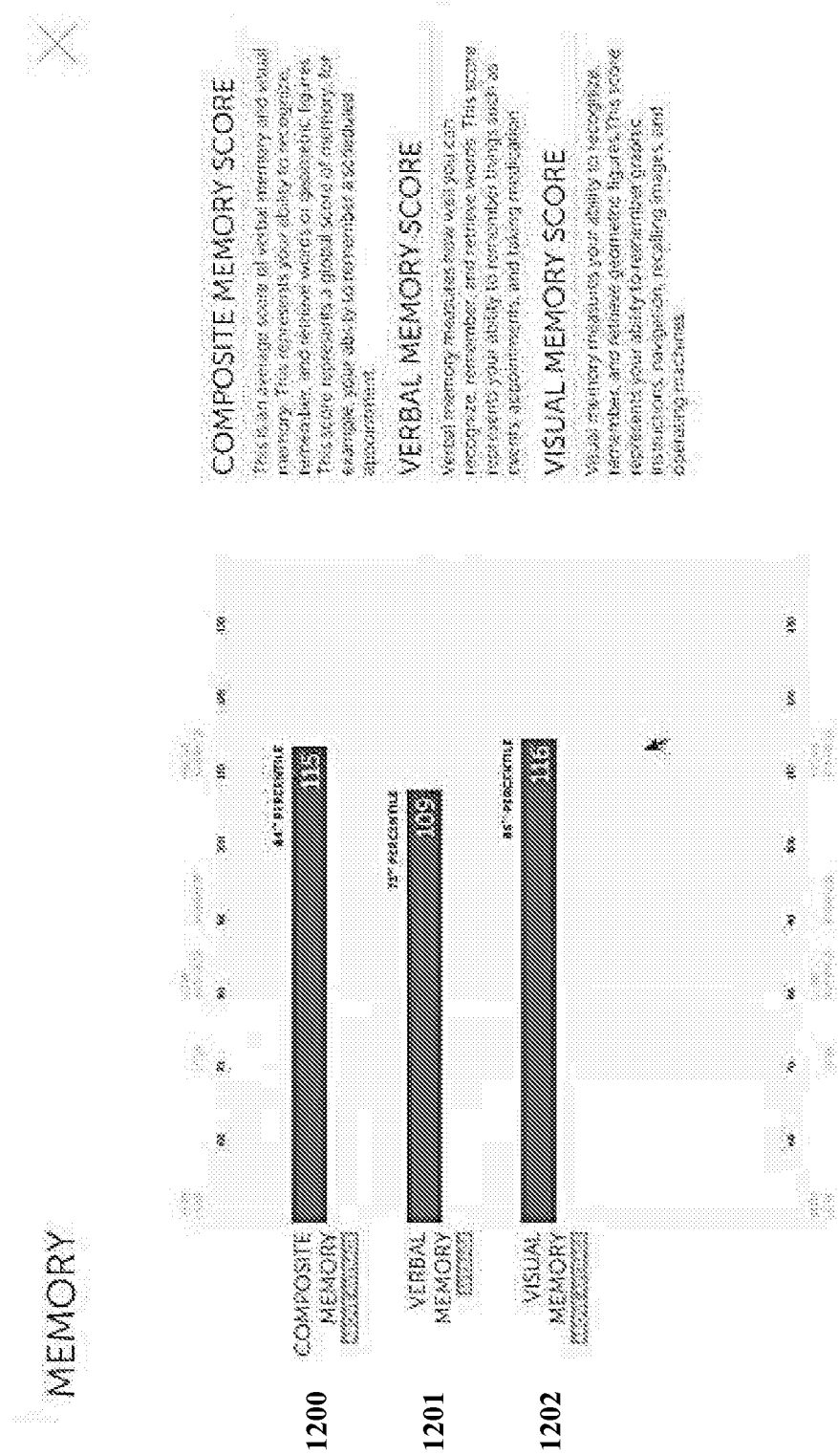
FIG. 12 shows a non-limiting example of a subcategory of health information; in this case, a summary of memory testing data.

Referring to FIG. 12, in a particular embodiment, memory testing health information is provided. In this case, test results for composite memory 1200, verbal memory 1201, and visual memory 1202 are provided. For each type of memory testing results, an overview is provided and a raw score and a percentile are indicated.

Figure 13:
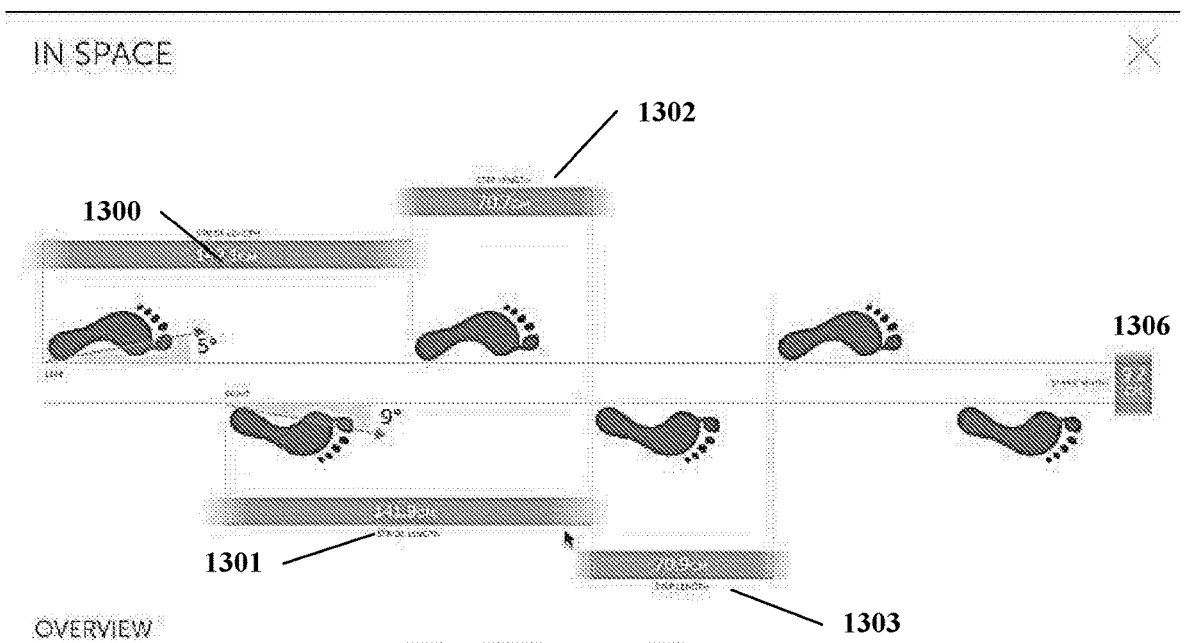
FIG. 13 shows a non-limiting example of a subcategory of health information; in this case, a summary of gait analysis data.

Referring to FIG. 13, in a particular embodiment, gait analysis health information is provided. In this case, an overview is provided as well as stride length for the left 1300 and right legs 1301, step lengths for the left 1302 and right 1303 legs, and foot angle for the left 1304 and right 1305 feet. Finally, an average step width 1306 is indicated.

Figure 14:
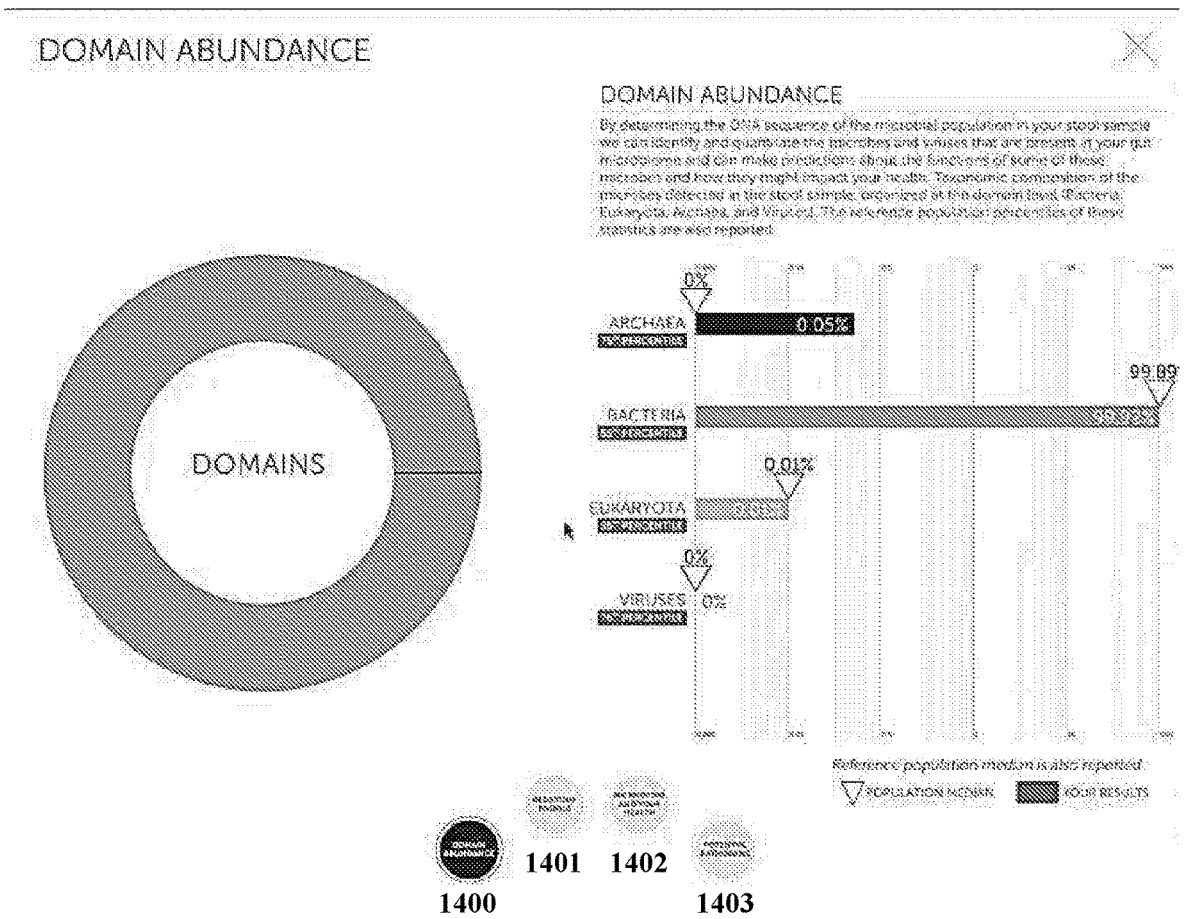
FIG. 14 shows a non-limiting example of a subcategory of health information; in this case, a summary of microflora population data.

Referring to FIG. 14, in a particular embodiment, microbiomic health information is provided. In this case, an overview is provided as well domain abundance for each of archaea, bacteria, eukaryotes, and viruses (in both bar chart and pie chart forms). In this case, bacteria made up 99.92% of the microbial population in the stool sample of the individual compared to 99.89% in the relevant population. Archea made up 0.05% of the microbial population in the stool sample of the individual compared to 0% in the relevant population. Eukaryotes made up 0.01% of the microbial population in the stool sample of the individual compared to 0.01% in the relevant population. And, viruses made up 0% of the microbial population in the stool sample of the individual compared to 0% in the relevant population. In this embodiment, the interface includes navigational elements allowing a user to access not only domain abundance information 1400, but also resistome profile information 1401, microbiome health information 1402, and potential pathogen information 1403.

Figure 15:
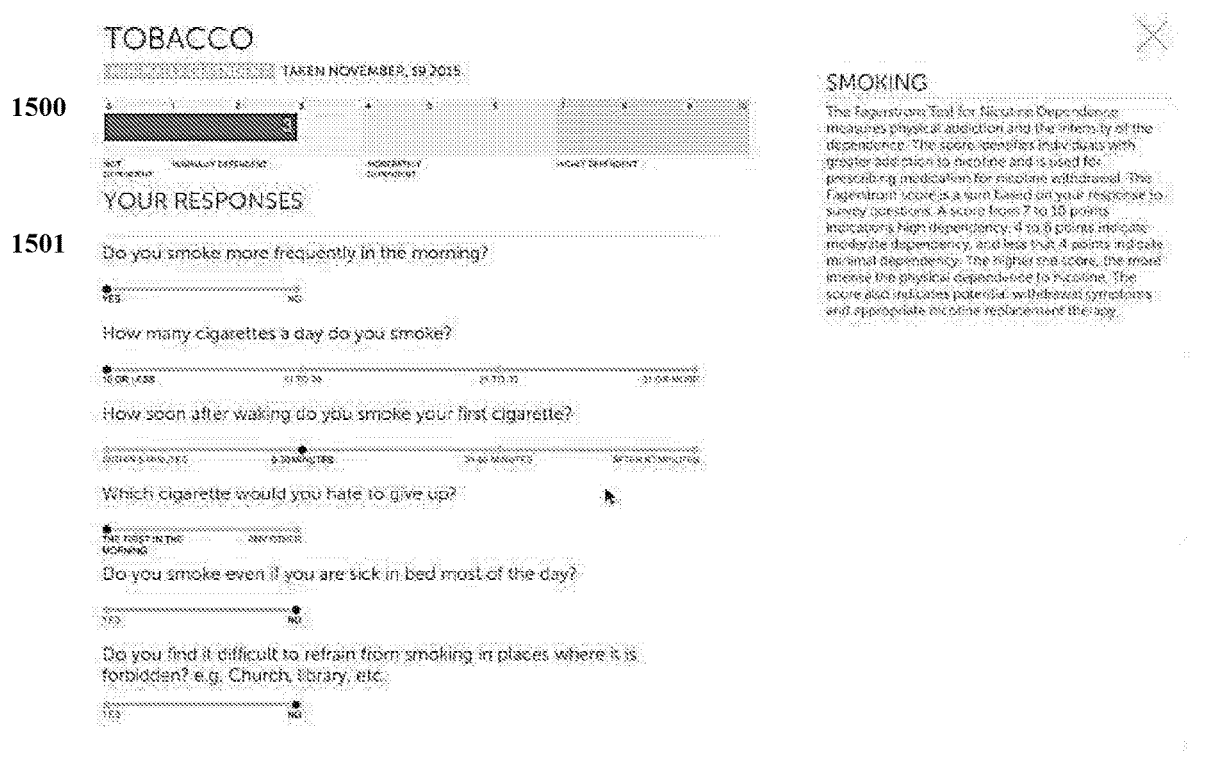

Referring to FIG. 15, in a particular embodiment, survey response health information is provided. In this case, health information based on the results of a survey regarding tobacco use, which are used to perform the Fagerstrom Test for nicotine dependence. The survey response health information includes an overview, a nicotine dependence score 1500, and the survey questions and their associated responses provided by the individual 1501.

Figure 16:
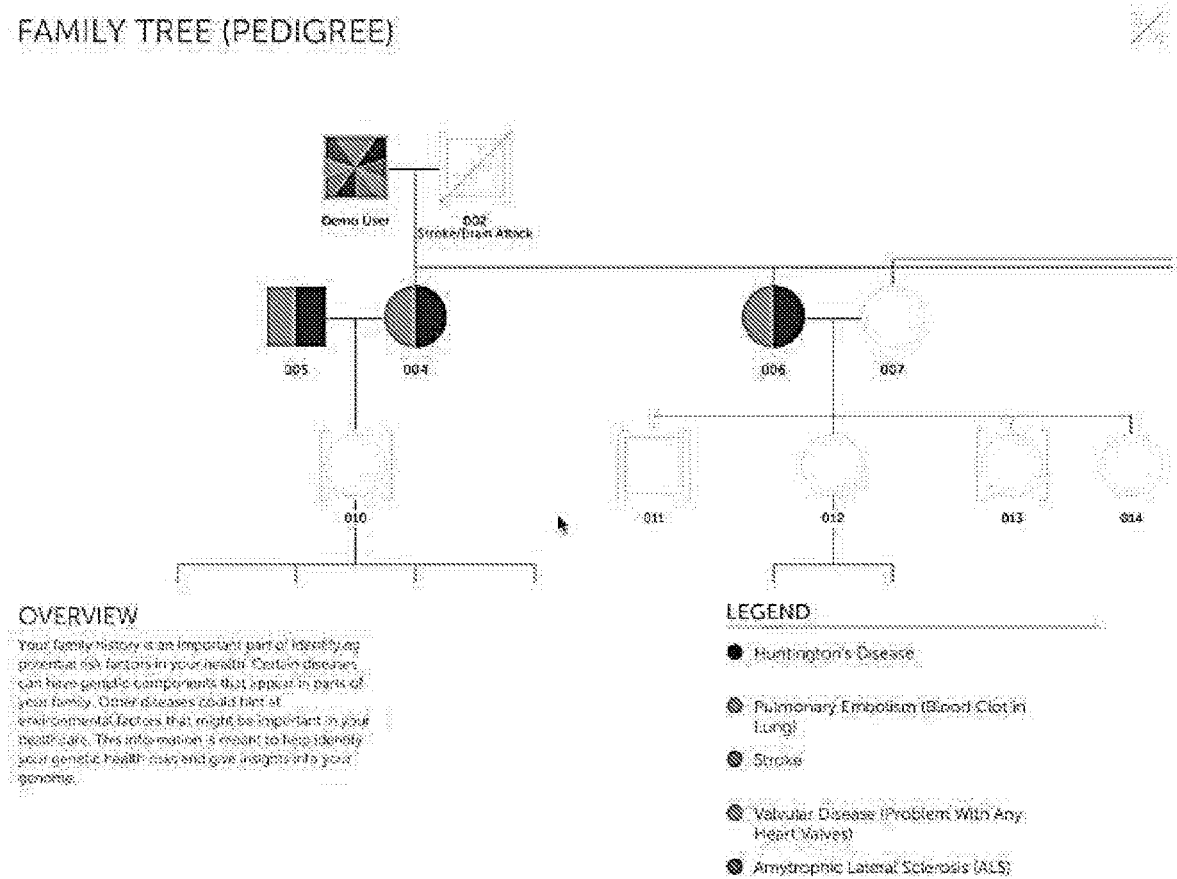
FIG. 16 shows a non-limiting example of a subcategory of health information; in this case, a family pedigree diagram.

Referring to FIG. 16, in a particular embodiment, family pedigree health information is provided. In this case, a family pedigree including health conditions and causes of death for family members.

Figure 17:
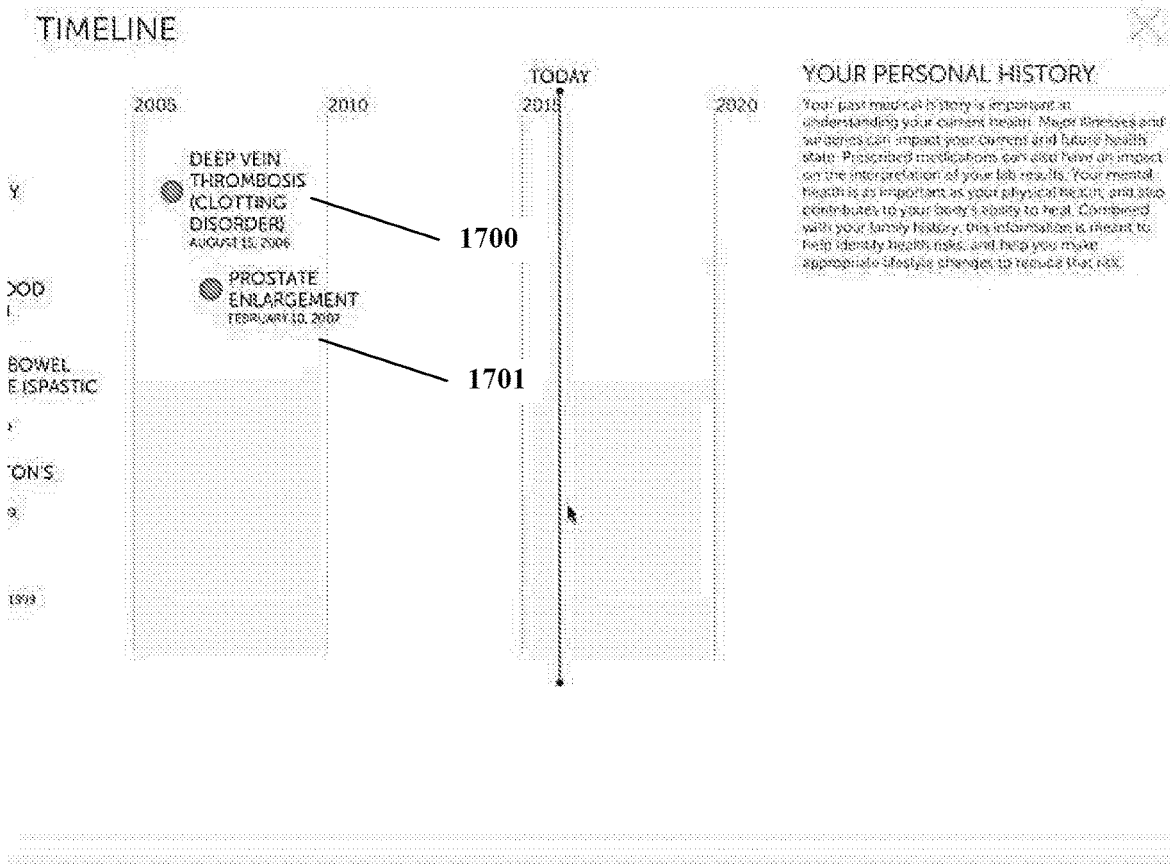
FIG. 17 shows a non-limiting example of a subcategory of health information; in this case, a personal heath history timeline.

Referring to FIG. 17, in a particular embodiment, health information is provided in the form of a health event timeline for an individual. In this case, a health event timeline including an overview and a plurality of health events mapped on a horizontal timescale with the present time indicate with a vertical line. The health events for the individual include a clotting disorder (deep vein thrombosis or DVT) 1700, diagnosed in 2006, and prostate enlargement 1701, diagnosed in 2007. A health event timeline optionally includes health information for family members of the individual.

The health information may take the form of a comprehensive health report comprising some or all of the information disclosed herein.

Slider Element

The platforms, systems, media, and methods described herein may include a slider GUI element, or use of the same. The slider GUI element allows the individual to select the current scale or scope of the health information they are interested in viewing. The slider element optionally includes scales larger than the individual, including regions and groups of people, and scales smaller than the individual, including organ systems, organs, and molecules within the individual. For example, in a particular implementation, the slider is graduated (from top to bottom) as follows:

Global ancestry;
Regional ancestry;
Extended family;
Immediate family;
Individual;
Biologic system;
Cells;
Chromosomes;
Genes; and
Gene variants.

Adjusting the slider element may change the scope/scale of the health information presented or available for navigation and viewing.

Digital Processing Device

The platforms, systems, media, and methods described herein may include a digital processing device, or use of the same. The digital processing device includes one or more hardware central processing units (CPUs) or general purpose graphics processing units (GPGPUs) that carry out the device's functions. The digital processing device further comprises an operating system configured to perform executable instructions. The digital processing device may be reversibly connected a computer network. In various embodiments, the digital processing device is optionally and reversibly connected to: the Internet such that it accesses the World Wide Web, a cloud computing infrastructure, an intranet, and/or a data storage device.

In accordance with the description herein, suitable digital processing devices include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

The digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, Roku®, Boxee®, Google TV®, Google Chromecast®, Amazon Fire®, and Samsung® HomeSync®. Those of skill in the art will also recognize that suitable video game console operating systems include, by way of non-limiting examples, Sony® PS3®, Sony® PS4®, Microsoft® Xbox 360®, Microsoft Xbox One, Nintendo® Wii °, Nintendo® Wii U®, and Ouya®.

The digital processing device includes a storage and/or memory device. The storage and/or memory device is one or more physical apparatuses used to store data or programs on a temporary or permanent basis. In some embodiments, the device is volatile memory and requires power to maintain stored information. In some cases, the memory device is non-volatile memory and retains stored information when the digital processing device is not powered. In various embodiments, the non-volatile memory comprises: flash memory, dynamic random-access memory (DRAM), ferroelectric random access memory (FRAM), and/or phase-change random access memory (PRAM). In other cases, the memory device is a storage device including, by way of non-limiting examples, CD-ROMs, DVDs, flash memory devices, magnetic disk drives, magnetic tapes drives, optical disk drives, and cloud computing based storage. The storage and/or memory device may be a combination of memory devices such as those disclosed herein.

The digital processing device optionally includes a display to send visual information to a user. Many types of display are suitable including, by way of examples, liquid crystal displays (LCD), thin film transistor liquid crystal displays (TFT-LCD), organic light emitting diode (OLED) displays (including passive-matrix OLED (PMOLED) and/or active-matrix OLED (AMOLED) displays), and plasma displays. In some cases, the display is a touchscreen or multi-touchscreen display. Other suitable displays include video projectors and head-mounted displays in communication with the digital processing device, such as a VR headset. Suitable VR headsets include, by way of non-limiting examples, HTC Vive, Oculus Rift, Samsung Gear VR, Microsoft HoloLens, Razer OSVR, FOVE VR, Zeiss VR One, Avegant Glyph, Freefly VR headset, and the like. The display may be one or more displays and include a combination of devices such as those disclosed herein.

The digital processing device optionally includes an input device to receive information from a user. In various embodiments, the input device is: a keyboard, a pointing device including, by way of non-limiting examples, a mouse, trackball, track pad, joystick, game controller, or stylus, a touch screen or a multi-touch screen, a microphone to capture voice or other sound input, and/or a video camera or other sensor to capture motion or visual input. In a particular embodiment, the input device is a Kinect, Leap Motion, or the like. The input device may a combination of devices such as those disclosed herein.

Figure 18:
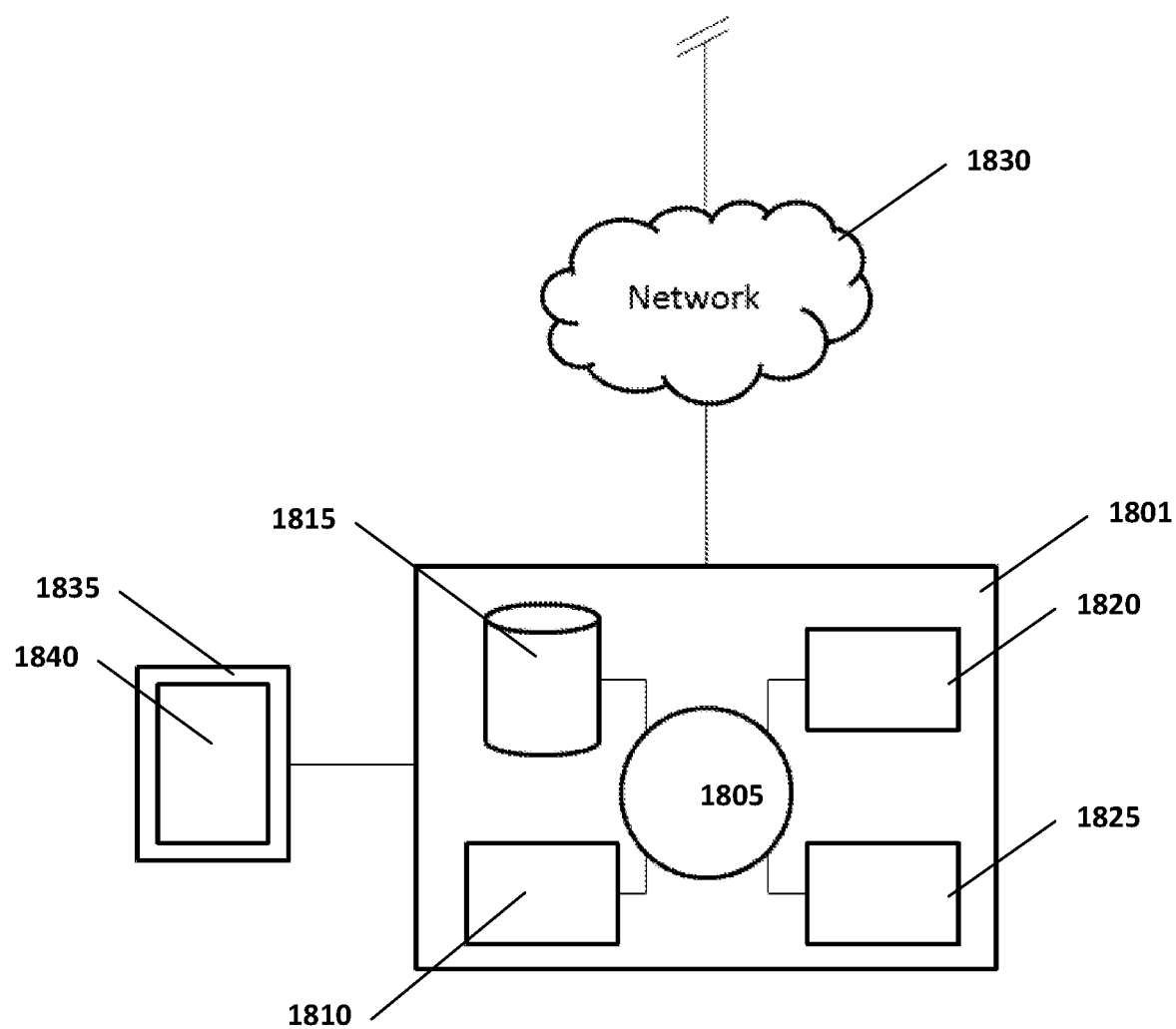
FIG. 18 shows a non-limiting example of a digital processing device; in this case, a device with one or more CPUs, a memory, a communication interface, and a display.

Referring to FIG. 18, in a particular embodiment, an exemplary digital processing device 1801 is programmed or otherwise configured to provide a display of an animated three-dimensional avatar of the individual and providing one or more navigational modes selected from: a list navigational mode, a two-dimensional map navigational mode, a three-dimensional landscape navigational mode, and a collage navigational mode. The device 1801 can regulate various aspects of the navigational modes of the present disclosure, such as, for example, displaying GUI elements for a current navigational mode and switching between navigational modes. In this embodiment, the digital processing device 1801 includes a central processing unit (CPU, also "processor" and "computer processor" herein) 1805, which can be a single core or multi core processor, or a plurality of processors for parallel processing. The digital processing device 1801 also includes memory or memory location 1810 (e.g., random-access memory, read-only memory, flash memory), electronic storage unit 1815 (e.g., hard disk), communication interface 1820 (e.g., network adapter) for communicating with one or more other systems, and peripheral devices 1825, such as cache, other memory, data storage and/or electronic display adapters. The memory 1810, storage unit 1815, interface 1820 and peripheral devices 1825 are in communication with the CPU 1805 through a communication bus (solid lines), such as a motherboard. The storage unit 1815 can be a data storage unit (or data repository) for storing data. The digital processing device 1801 can be operatively coupled to a computer network ("network") 1830 with the aid of the communication interface 1820. The network 1830 can be the Internet, an internet and/or extranet, or an intranet and/or extranet that is in communication with the Internet. The network 1830 in some cases is a telecommunication and/or data network. The network 1830 can include one or more computer servers, which can enable distributed computing, such as cloud computing. The network 1830, in some cases with the aid of the device 1801, can implement a peer-to-peer network, which may enable devices coupled to the device 1801 to behave as a client or a server.

Continuing to refer to FIG. 18, the CPU 1805 can execute a sequence of machine-readable instructions, which can be embodied in a program or software. The instructions may be stored in a memory location, such as the memory 1810. The instructions can be directed to the CPU 1805, which can subsequently program or otherwise configure the CPU 1805 to implement methods of the present disclosure. Examples of operations performed by the CPU 1805 can include fetch, decode, execute, and write back. The CPU 1805 can be part of a circuit, such as an integrated circuit. One or more other components of the device 1801 can be included in the circuit. In some cases, the circuit is an application specific integrated circuit (ASIC) or a field programmable gate array (FPGA).

Continuing to refer to FIG. 18, the storage unit 1815 can store files, such as drivers, libraries and saved programs. The storage unit 1815 can store user data, e.g., user preferences and user programs. The digital processing device 1801 in some cases can include one or more additional data storage units that are external, such as located on a remote server that is in communication through an intranet or the Internet.

Continuing to refer to FIG. 18, the digital processing device 1801 can communicate with one or more remote computer systems through the network 1830. For instance, the device 1801 can communicate with a remote computer system of a user. Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants.

Methods as described herein can be implemented by way of machine (e.g., computer processor) executable code stored on an electronic storage location of the digital processing device 1801, such as, for example, on the memory 1810 or electronic storage unit 1815. The machine executable or machine readable code can be provided in the form of software. During use, the code can be executed by the processor 1805. In some cases, the code can be retrieved from the storage unit 1815 and stored on the memory 1810 for ready access by the processor 1805. In some situations, the electronic storage unit 1815 can be precluded, and machine-executable instructions are stored on memory 1810.

Non-Transitory Computer Readable Storage Medium

The platforms, systems, media, and methods disclosed herein may include one or more non-transitory computer readable storage media encoded with a program including instructions executable by the operating system of an optionally networked digital processing device. The computer readable storage medium may be a tangible component of the digital processing device, which may be optionally removable from the digital processing device. Many types of media are suitable to store the instructions. In various embodiments, suitable computer readable storage medium include, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

The platforms, systems, media, and methods disclosed herein may include one or more computer programs, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, those of skill in the art will recognize that a computer program may be written in various versions of various languages.

The functionality of the computer readable instructions may be combined or distributed as desired in various environments. In some cases, a computer program comprises one sequence of instructions. In other cases, a computer program comprises a plurality of sequences of instructions. In some cases, a computer program is provided from one location. In other cases, a computer program is provided from a plurality of locations. In various embodiments, a computer program includes, in part or in whole, one or more software modules, one or more web applications, one or more mobile applications, one or more standalone applications, one or more web browser plug-ins, extensions, add-ins, or add-ons, or combinations thereof.

Web Application

A computer program may comprise a web application. In light of the disclosure provided herein, those of skill in the art will recognize that a web application, in various embodiments, utilizes one or more software frameworks and one or more database systems. A web application is optionally created on a software framework such as Microsoft® .NET or Ruby on Rails (RoR). A web application optionally utilizes one or more database systems including, by way of non-limiting examples, relational, non-relational, object oriented, associative, and XML database systems. Suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some cases, a web application is written to some extent in a markup language such as Hypertext Markup Language (HTML), Extensible Hypertext Markup Language (XHTML), or eXtensible Markup Language (XML). In some cases, a web application is written to some extent in a presentation definition language such as Cascading Style Sheets (CSS). In some cases, a web application is written to some extent in a client-side scripting language such as Asynchronous Javascript and XML (AJAX), Flash® Actionscript, Javascript, or Silverlight. In some cases, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some cases, a web application is written to some extent in a database query language such as Structured Query Language (SQL). A web application may include a media player element, which utilizes one or more of many suitable multimedia technologies including, by way of non-limiting examples, Adobe® Flash®, HTML 5, Apple® QuickTime®, Microsoft® Silverlight®, Java™, and Unity®.

Figure 19:
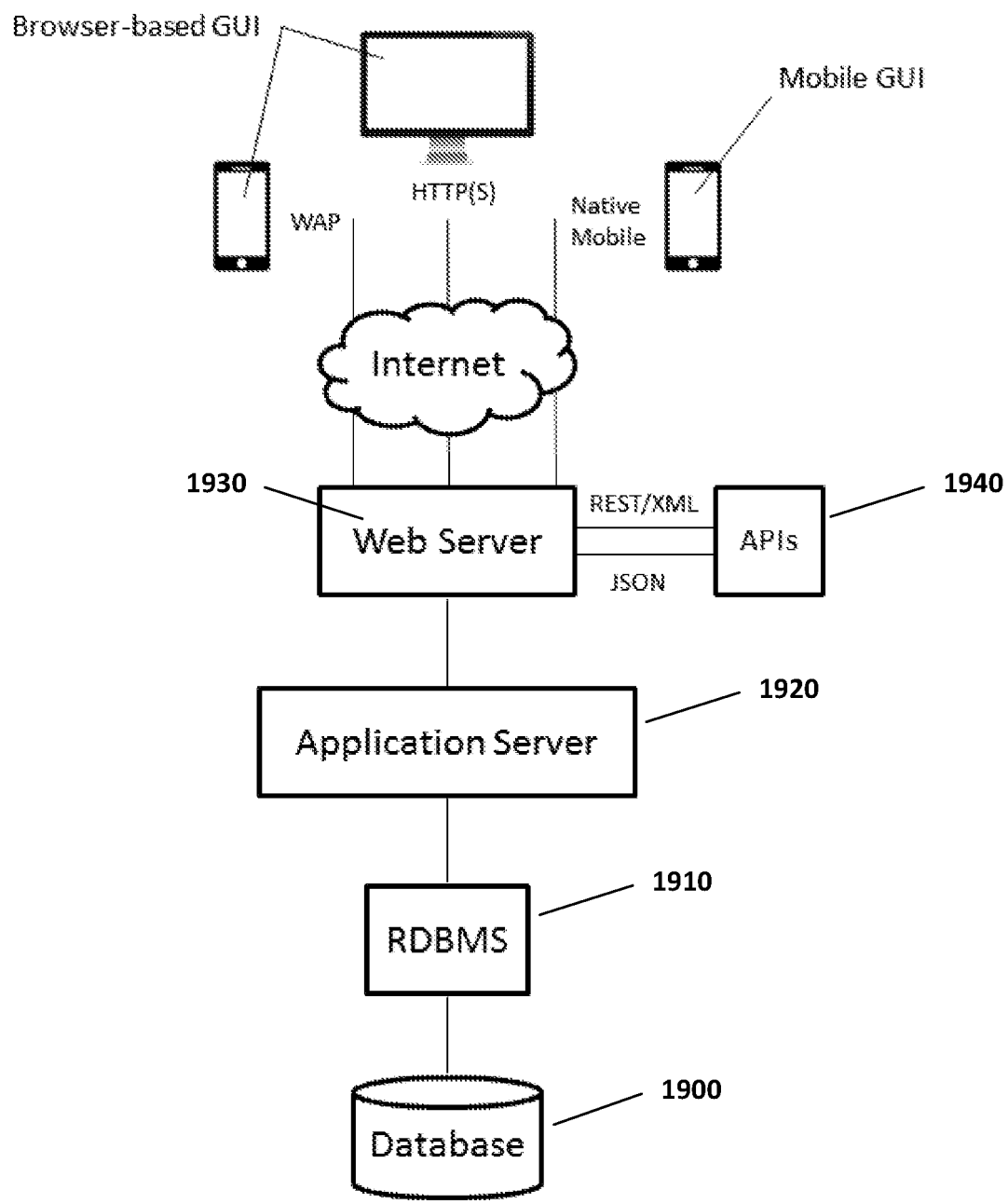
FIG. 19 shows a non-limiting example of a web/mobile application provision system; in this case, a system providing browser-based and/or native mobile user interfaces.

Referring to FIG. 19, in a particular embodiment, an application provision system comprises one or more databases 1900 accessed by a relational database management system (RDBMS) 1910. Suitable RDBMSs include Firebird, MySQL, PostgreSQL, SQLite, Oracle Database, Microsoft SQL Server, IBM DB2, IBM Informix, SAP Sybase, SAP Sybase, Teradata, and the like. In this embodiment, the application provision system further comprises one or more application severs 1920 (such as Java servers, .NET servers, PHP servers, and the like) and one or more web servers 1930 (such as Apache, IIS, GWS and the like). The web server(s) optionally expose one or more web services via app application programming interfaces (APIs) 1940. Via a network, such as the Internet, the system provides browser-based and/or mobile native user interfaces.

Figure 20:
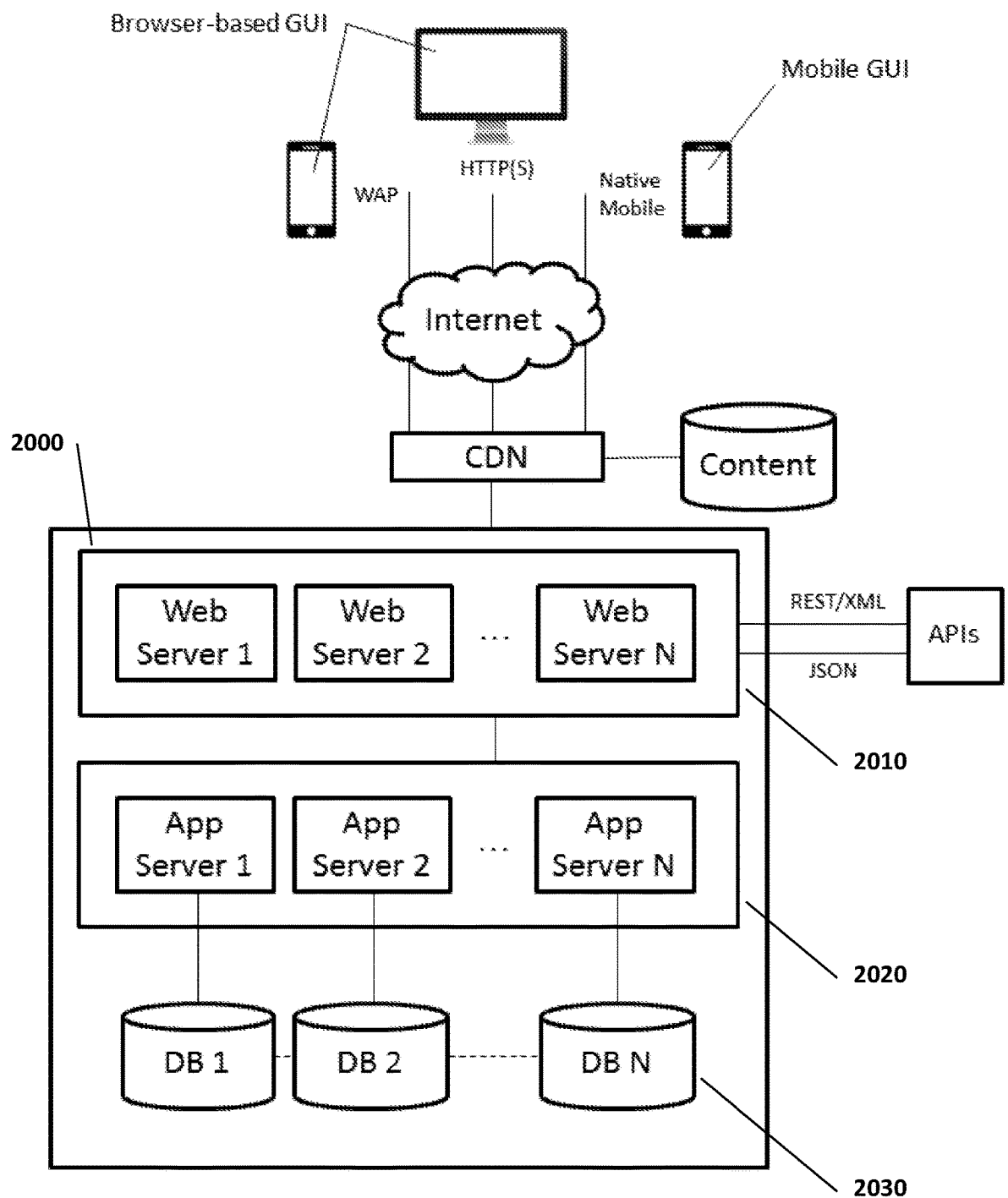
FIG. 20 shows a non-limiting example of a cloud-based web/mobile application provision system; in this case, a system comprising an elastically load balanced, auto-scaling web server and application server resources as well synchronously replicated databases.

Referring to FIG. 20, in a particular embodiment, an application provision system alternatively has a distributed, cloud-based architecture 2000 and comprises elastically load balanced, auto-scaling web server resources 2010 and application server resources 2020 as well synchronously replicated databases 2030.

Mobile Application

A computer program may comprise a mobile application provided to a mobile digital processing device. The mobile application may be provided to a mobile digital processing device at the time it is manufactured or via the computer network described herein subsequent to manufacture. In view of the disclosure provided herein, a mobile application is created by techniques known to those of skill in the art using hardware, languages, and development environments known to the art. Those of skill in the art will recognize that mobile applications are written in several languages. Suitable programming languages include, by way of non-limiting examples, C, C++, C #, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome Web Store, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

A computer program may comprise a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some cases, a computer program includes one or more executable complied applications.

Web Browser Plug-in

A computer program may comprise a web browser plug-in (e.g., extension, etc.). In computing, a plug-in is one or more software components that add specific functionality to a larger software application. Makers of software applications support plug-ins to enable third-party developers to create abilities which extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®.

In view of the disclosure provided herein, those of skill in the art will recognize that several plug-in frameworks are available that enable development of plug-ins in various programming languages, including, by way of non-limiting examples, C++, Delphi, Java™ PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon Kindle® Basic Web, Nokia® Browser, Opera Software® Opera® Mobile, and Sony® PSP™ browser.

Software Modules

The platforms, systems, media, and methods disclosed herein may include one or more software, server, and/or database modules, or use of the same. In view of the disclosure provided herein, software modules are created by techniques known to those of skill in the art using machines, software, and languages known to the art. The software modules disclosed herein are implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules comprise, by way of non-limiting examples, a web application, a mobile application, and a standalone application. In some embodiments, software modules are in one computer program or application. In other embodiments, software modules are in more than one computer program or application. In some embodiments, software modules are hosted on one machine. In other embodiments, software modules are hosted on more than one machine. In further embodiments, software modules are hosted on cloud computing platforms. In some embodiments, software modules are hosted on one or more machines in one location. In other embodiments, software modules are hosted on one or more machines in more than one location.

Databases

The platforms, systems, media, and methods disclosed herein may include one or more databases, or use of the same. In view of the disclosure provided herein, those of skill in the art will recognize that many databases are suitable for storage and retrieval of patient, health, and navigational mode information. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database is web-based. In still further embodiments, a database is cloud computing-based. In other embodiments, a database is based on one or more local computer storage devices.

EXAMPLES

The following illustrative examples are representative of embodiments of the software applications, systems, media, and methods described herein and are not meant to be limiting in any way.

Example 1—Researching Cancer Risks and Prevention

Bob is a middle aged man with a family history of cancer is interested in understanding his personal risks of serious disease. He is also interested in learning more about interventions that may be tailored to his risk profile that may reduce his risk of cancer. Bob does not have any background in genetics or medicine, but is determined to fully understand his personal risks and lifestyle recommendations that could improve his health and that of his family. Bob, in light of his motivation and high level of interest, decides to have his genome sequenced, his metabolome and microbiome analyzed, and to invest in a computer-implemented interactive health portal to view and dissect the implications of the trove of resulting health information.

Bob visits a clinic to supply biological samples and to have medical imaging performed. These procedures also include three-dimensional imaging of Bob to generate a personalized avatar. Once the results of his medical testing are available, Bob receives a consultation and explanation of his results by a medical professional and returns home to review the results in detail on his mobile tablet computer.

He logs into his electronic health portal that displays the results of his genomic, metabolomic, and microbiomic testing. Bob is greeted at his health portal by an animated three-dimensional avatar of himself, which provides a short introduction to how to access the various categories and subcategories therein through the navigational modes. The avatar is lifelike and animated depicting Bob in various states of activity.

As a non-scientist who is relatively unfamiliar with computers and computing applications, Bob feels comforted by, and can better understand the instructions spoken through, his avatar. Bob appreciates that the navigation is performed through a personalized medium that is more private and personalized than a video, image, or avatar of a generic doctor or health care practitioner.

Bob experiments with multiple navigational modes offered by his health portal to determine which mode for navigating and reviewing his health information, including the results of his genomic, metabolomic, and microbiomic testing, is most intuitive for him.

Bob first selects a collage navigational mode, which shows a collage of icons or pictures with labels, each representing a category of health information. Bob then tries a two-dimensional map navigational mode, where he sees several navigational elements including icons, text, and pictures which represent categories and subcategories of his health information arranged circularly around his avatar. Finally, Bob enables a list navigation mode. He finds the hierarchical listing of all the categories and subcategories easy to read and navigate. As a result, Bob is able to quickly understand the large amount of complex health information communicated via his health portal.

Confident in his abilities to navigate through his sensitive medical information, Bob traverses and reviews each category of health information as summarized in text, images, two-dimensional and three-dimensional maps, graphs, and charts, videos, interactive sequence listings, and the like, at his portal. He reviews definitions and additional information to further research and understand his health information.

Example 2—Researching Cancer Risks and Prevention

Sarah is a teenager who is interested in studying her family history. Although she has heard many stories from her family about her past, she is curious to learn more about her genetic ancestry. Sarah visits a clinic to supply biological samples and to have medical imaging performed. These procedures also include three-dimensional imaging of Sarah, via multiple cameras, to generate a personalized avatar. Once the results of his medical testing are available, Sarah reviews her results in detail from her home laptop computer.

Although Sarah is a good student in school, she understands that there are many aspects of health and genomics that are unfamiliar to her. After logging in to a personalized electronic health portal, Sarah is pleased to be greeted by an avatar that strongly resembles her, which feels personalized and approachable.

Sarah first tries several navigational modes offered by her health portal to determine which mode for navigating and displaying her voluminous health information, including results of her genomic, metabolomic, and microbiomic testing, is the most interesting and fun. Sarah first tries a list navigational mode and finds it easy to view all the components of her health information in a hierarchical list. However, she is excited that an alternative three-dimensional navigation mode feels more like playing some of her favorite video games.

Sarah then finds, and clicks on the "Ancestry" subcategory within the "Genome" category where she finds a color coded map of her maternal and paternal descendants. After reviewing her family history, Sarah becomes curious about the other aspects of her health information and returns to her home page to review additional three-dimensional and two-dimensional representations of her health. Sarah clicks on the "Physical Traits Overview" subcategory within the "Genome" category where she is presented with representations of how her unique genome affects such physical attributes as her hair curls and her freckles. Sarah also explores a pedigree tree which displays how she has inherited various risks of disease. Sarah clicks on several unfamiliar terms to view descriptions and pictures that define the attribute or DNA related terms. Sarah also reviews physical and cognitive data collected at the clinic including her body composition, gait, bone density, and memory analysis.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

What is claimed is:

1. A computer-implemented system comprising: a digital processing device comprising: at least one processor, an operating system configured to perform executable instructions, a memory, and a computer program including instructions executable by the digital processing device to create an interactive health portal for presentation of health information of an individual comprising:
    a) a software module providing a display of an animated three-dimensional avatar of the individual, the avatar generated by three-dimensional imaging of the individual's person; and
    b) one or more software modules providing at least one of the following distinct navigational modes for navigating a plurality of categories of health information, each category having at least one subcategory of health information, the modes comprising:
        i) a list navigational mode displaying text elements representing the categories and the subcategories, the text elements arranged hierarchically to represent the relationship between the categories and the subcategories;
        ii) a two-dimensional map navigational mode displaying icon elements representing the categories arranged circularly and displaying icon elements representing the subcategories arranged circularly around the icon elements representing the categories to represent the relationship between the categories and the subcategories; and
        iii) a three-dimensional landscape navigational mode displaying the avatar in a three-dimensional landscape with regions representing the categories and the subcategories;
        wherein each navigational mode comprises an element to navigate to the display of the avatar, and wherein the individual can switch between the navigational modes.
2. The system of claim 1, wherein the navigational modes further comprise a collage mode displaying a collage of icons representing the subcategories around the display of the avatar.
3. The system of claim 1, wherein the interactive health portal comprises one or more software modules providing at least two of the distinct navigational modes.
4. The system of claim 1, wherein the interactive health portal comprises one or more software modules providing at least three of the distinct navigational modes.
5. The system of claim 1, wherein the categories of health information comprise laboratory test results, survey results, medical imaging results, genomic analysis results, and sensor data.
6. The system of claim 1, wherein the navigational modes are used via a touchscreen or multi-touchscreen.
7. A non-transitory computer-readable storage media encoded with a computer program including instructions executable by a processor to create an interactive health portal for presentation of health information of an individual comprising:
    a) a software module providing a display of an animated three-dimensional avatar of the individual, the avatar generated by three-dimensional imaging of the individual's person; and
    b) one or more software modules providing at least one of the following distinct navigational modes for navigating a plurality of categories of health information, each category having at least one subcategory of health information, the modes comprising:
        i) a list navigational mode displaying text elements representing the categories and the subcategories, the text elements arranged hierarchically to represent the relationship between the categories and the subcategories;
        ii) a two-dimensional map navigational mode displaying icon elements representing the categories arranged circularly and displaying icon elements representing the subcategories arranged circularly around the icon elements representing the categories to represent the relationship between the categories and the subcategories; and
        iii) a three-dimensional landscape navigational mode displaying the avatar in a three-dimensional landscape with regions representing the categories and the subcategories;
        wherein each navigational mode comprises an element to navigate to the display of the avatar, and wherein the individual can switch between the navigational modes.
8. The media of claim 7, wherein the navigational modes further comprise a collage mode displaying a collage of icons representing the subcategories around the display of the avatar.
9. The media of claim 7, wherein the interactive health portal comprises one or more software modules providing at least two of the distinct navigational modes.
10. The media of claim 7, wherein the interactive health portal comprises one or more software modules providing at least three of the distinct navigational modes.
11. The media of claim 7, wherein the categories of health information comprise laboratory test results, survey results, medical imaging results, genomic analysis results, and sensor data.
12. The media of claim 7, wherein the navigational modes are used via a touchscreen or multi-touchscreen.
13. A computer-implemented method of providing an interactive health portal for presentation of health information of an individual, the method comprising:
    a) displaying, by a computer, an animated three-dimensional avatar of the individual, the avatar generated by three-dimensional imaging of the individual's person; and b) providing, by the computer, at least one of the following distinct navigational modes for navigating a plurality of categories of health information, each category having at least one subcategory of health information, the modes comprising:
  i) a list navigational mode displaying text elements representing the categories and the subcategories, the text elements arranged hierarchically to represent the relationship between the categories and the subcategories;
  ii) a two-dimensional map navigational mode displaying icon elements representing the categories arranged circularly and displaying icon elements representing the subcategories arranged circularly around the icon elements representing the categories to represent the relationship between the categories and the subcategories; and
  iii) a three-dimensional landscape navigational mode displaying the avatar in a three-dimensional landscape with regions representing the categories and the subcategories;

wherein each navigational mode comprises an element to navigate to the display of the avatar, and wherein the individual can switch between the navigational modes.

14. The method of claim 13, wherein the navigational modes further comprise a collage mode displaying a collage of icons representing the subcategories around the display of the avatar.

15. The method of claim 13, comprising providing, by the computer, at least two of the distinct navigational modes.

16. The method of claim 13, comprising providing, by the computer, at least three of the distinct navigational modes.

17. The method of claim 13, wherein the categories of health information comprise laboratory test results, survey results, medical imaging results, genomic analysis results, and sensor data.

18. The method of claim 13, wherein the navigational modes are used via a touchscreen or multi-touchscreen.

* * * * *